United States Patent [19]

McConnel

[11] Patent Number: 5,024,240
[45] Date of Patent: Jun. 18, 1991

[54] MANOFLUOROGRAPHY SYSTEM, METHOD FOR FORMING A MANOFLUOROGRAM AND METHOD FOR PREPARING A SWALLOWING PROFILE

[76] Inventor: Fred M. S. McConnel, 180 Blackland Dr., Atlanta, Ga. 30342

[21] Appl. No.: 293,049

[22] Filed: Jan. 3, 1989

[51] Int. Cl.$^5$ .............................................. A61B 5/103
[52] U.S. Cl. ..................................... 128/780; 128/748
[58] Field of Search ....................... 128/748, 774, 780; 364/413.02, 413.13

[56] References Cited

U.S. PATENT DOCUMENTS

| | | | |
|---|---|---|---|
| 4,517,984 | 5/1985 | Perlin | 128/642 |
| 4,561,450 | 12/1985 | Bryant | 128/780 |
| 4,815,472 | 3/1989 | Wise et al. | 128/748 |

OTHER PUBLICATIONS

Kaye et al., "Medical Research Engineering", vol. 12, No. 5, Nov. 1977, pp. 10–15.
E. M. Sokol et al., Simultaneous Cinoradiographic and Manometric Study of the Pharynx, Hypopharynx and Cervical Esophagus, 51, Gastroenterology, 960–974 (1966).
W. J. Dodds et al., Quantition of Pharyngeal Motor Function in Normal Human Subjects, 39, J. Appl. Physiol., 692–696 (1975).
J. Orlowski et al., Requirements for Accurate Manometer Recording of Pharyngeal and Esophageal Peristaltic Pressure Waves, 17, Invest. Radiol., 567–572 (1982).
F. M. S. McConnel et al., Examination of Swallowing After Total Laryngectomy Using Manofluorography, 8, Head Neck Surg. J., 3–12 (1986).
F. M. S. McConnel, Manofluorography of Deglutition After Supraglottic Laryngectomy, 9, Neck Surg. J., 142–150 (1986).
F. M. S. McConnel et al., Function of the Pharyngoesophageal Segment, 97, Laryngoscope, 483–489 (1987).
R. W. Welch et al., Manometry of the Normal Upper Esophageal Sphincter and Its Alterations in Laryngectomy, 63, J. Clin. Invest., 1036–1041 (1979).
A. Isberg et al., Movement of the Upper Esophageal Sphincter and a Manometric Device During Deglutition, 26, Act Radiol. [DIAG] (Stockh), 381–388 (1985).
A. Isberg et al., The Upper Esophageal Sphincter During Normal Deglutition, 26, Act Radiol [DIAG] (Stockh), 563–568 (1985).
W. J. Dodds et al., Considerations About Pharyngeal Manometry, 1, J. Dysphagia, 209–214 (1987).
F. M. S. McConnel, The Effects of Surgery on Pharyngeal Deglutition, 1, J. Dysphagia, 145–151 (1987).

Primary Examiner—William E. Kamm
Attorney, Agent, or Firm—Sutherland, Asbill & Brennan

[57] ABSTRACT

A system for quantifying pressure exerted on a bolus in a digestive tract of a patient includes: a catheter of sufficient length and insert into the digestive tract of the patient, a plurality of radiopaque pressure sensors on the catheter to output pressure data, a videofluoroscope for producing images of the digestive tract of the patient in which the bolus is moving in relation to the sensors, and equipment for recording a video record of a sequence of the images and the data, wherein the equipment combines each image with a substantially contemporaneous portion of the pressure data to form a video record sequence of images and the substantially contemporaneous portions of the pressure data.

The system produces a manofluorogram, which is a videotape record of the videofluoroscopic and contemporaneous pressure data, preferably with timing information. The system also produces a manofluorogram, which is an analysis of pressure data based on timing information derived from the videotape. A method of manufacture and method of use for the above are also set forth.

38 Claims, 14 Drawing Sheets

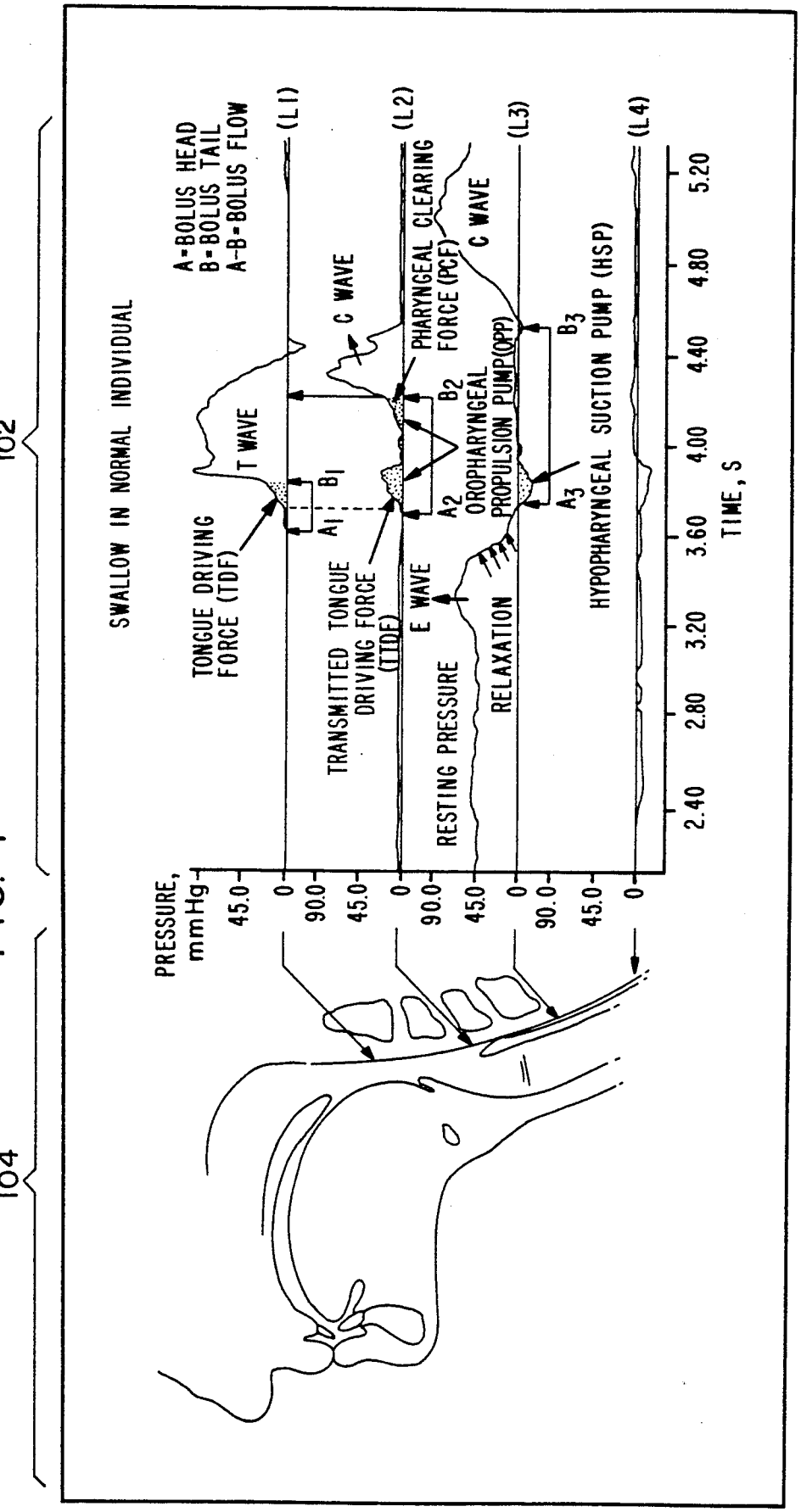

MANOFLUOROGRAPHY SYSTEM, METHOD FOR FORMING A MANOFLUOROGRAM AND METHOD FOR PREPARING A SWALLOWING PROFILE

BACKGROUND OF THE INVENTION

1. Field of Invention

The present invention relates to medical equipment used for examining swallowing, and, more particularly, to the use of this equipment to produce a manofluorograph and a monofluorogram to aid in the diagnosis and treatment of disorders in the digestive tract. The equipment combines pressure sensor measurements with contemporaneous videofluoroscopy of a patient swallowing a radiopaque bolus past the sensors on a catheter.

2. Description of the Related Art

Analyzing the physiology of swallowing has long been regarded as a challenge. So many events occur in such a rapid sequence that the prior art has not been able to precisely characterize source of pressure and quantify the amount of pressure applied to the bolus during swallowing.

Mere fluoroscopic analysis of a patient swallowing barium provides only superficial insights into the nature of swallowing and many problems associated therewith. Videofluoroscopy has provided more detail than fluoroscopic analysis, but equipment for time-framing is not built into the video recorders ordinarily used by radiology departments.

Manometry is rarely used to analyze events above the pharyngoesophageal (PE) segment. When manometry is used, it has been difficult to assign pressures to specific pharyngeal structures. E. M. Sokol, P. Heitman, B. S. Wolf, et al., Simultaneous Cino-Radiographic and Manometric Study of the Pharynx, Hypopharynx, and Cervical Esophagus, Gastroenterology, 960-974 (1966). Also, the pharynx has been difficult to evaluate through manometry because of rapid, precipitous pressure changes and the proximity of the airway. W. J. Dodds, W. J. Hogan, S. B. Lydon, et al., Quantitation of Pharyngeal Motor Function in Normal Human Subjects, J. Appl. Physiol. 692-696 (1975).

Most manometric measuring devices that have been used in the pharynx were developed for measuring the pressures of the esophagus. These instruments are inadequate for the dynamics of pharyngeal manometry because the pharynx and the esophagus are functionally different. The pharynx generates pressures of 200 to 400 mm Hg at rates of up to 4,000 mm Hg per second. Esophageal peristalsis is a much milder event. Esophageal pressures reach only 80 to 140 mm Hg at rates of 160 to 400 mm Hg per second. Pharyngeal waves travel at 9 to 25 cm per second, compared with 4 cm per second in the esophagus. Id. A flat frequency response rate of up to 5 Hz is required for manometry for esophageal pressure. J. Orlowski, W. J. Dodds, J. H. Linhan, et al., Requirements for Accurate Manometer Recording of Pharyngeal and Esophageal Peristaltic Pressure Waves, 17 Invest. Radiol. 567-572 (1982). The measurement of pharyngeal pressures requires a frequency response rate of up to 48 Hz. Investigators using infusion catheters to measure pharyngeal deglutition have reported questionably low pressure peaks of less than 100 mm Hg, suggesting inadequate manometer frequency response rates.

Previous attempts to examine swallowing by combining video fluoroscopy and manometry have involved water manometry: F. M. S. McConnel, M. S. Mendelsohn, J. A. Logemann, Examination of Swallowing After Total Laryngectomy Using Manofluorography, 8 Head Neck Surg. J. 3-12 (1986); F. M. S. McConnel, M. S. Mendelsohn, J. A. Logemann, Manofluorography of Deglutition After Supraglottic Laryngectomy, 9 Head Neck Surg. J. 142-150 (1986); and M. S. Mendelsohn, F. M. S. McConnel, Function of the Pharyno-Esophageal Segment, 97 Laryngoscope 483-489 (1987). Unlike solid state sensors, water manometric sensors have a time lag of about 0.1 second from the time of pressure initiation to its display. Due to this delay, the use of water manometers provides data that lags the videofluoroscopy pictures. Thus, combining of such data with simultaneously produced videofluoroscopy does not accurately portray swallowing.

A solid-state strain gauge can accurately measure pharyngeal pressure transients without the time lag of water sensors. These transducers have more appropriate frequency response rates and give high-fidelity recording of the precipitous pressure gradients. The newer gauges are more temperature-stable and less fragile than the previous semiconductor devices. The gauges can also be oriented to "look" in one direction.

Another of the difficulties in the measurement of pharyngeal pressure is the existence of radial pressure differences. Radial manometry at the cricopharyngeal area reveals a marked asymmetry, with pressures higher in the anteroposterior dimension than in the lateral dimension. R. W. Welch, K. Luckmann, P. M. Ricks, et al., Manometry of the Normal Upper Esophageal Sphineter and its Alterations in Laryngectomy, 63 J. Clin. Invest. 1036-1041 (1979).

Catheter movement has been thought to cause erroneous PE segment pressure measurements. PE segment elevation is 1.2 cm greater than the catheter elevation during normal deglutition. A. Isberg, M. E. Nilsson, H. Schiratzki, Movement of the Upper Esophageal Sphincter and a Manometric Device During Deglutition, 26 Act Radiol. [DIAGN] (Stockh) 381-388 (1985) and A. Isberg, M. E. Nilsson, H. Schiratzki, The Upper Esophageal/Sphincter During Normal Deglutition, 26 Act Radiol. [DIAGN] (Stockh) 563-568 (1985). See also W. J. Dodds, P. J. Kahalas, J. Dowd, and W. J. Hogan, Considerations about Pharyngeal Manometry, 1 J. Dysphagia 209-214 (1987). The catheter sensor can move out of the PE segment high-pressure zone. During a swallow, the rapid movement of the tongue, palate, larynx and pharyngeal walls occurs such that the level of each structure can change 1-3 cm. A catheter may also move this distance at the tongue or palate. Thus, it has been difficult to associate specific physiological events in the pharynx with pressure measurements and to determine the role that pressure changes play in bolus passage.

Among the studies which have combined fluoroscopy and manometry are the above referenced Isberg articles as well as Sokol, Id. Sokol and colleagues defined three different types of positive pharyngeal pressure waves: the E, T, and P waves. The E wave occurs in association with laryngopharyngeal elevation. The T wave onset coincides with backward movement of the tongue base. The third and largest positive wave was termed the P wave because it coincides with the peristaltic stripping wave visible by X-ray. In the classic description, the peristaltic wave starts at Passavant's ridge and travels down the pharynx.

In sum, the prior art has not precisely related measured pressures to the passage of the bolus to allow quantitative analysis of swallowing. Thus, diagnosis and treatment of swallowing disorders has been limited.

SUMMARY OF THE INVENTION

OBJECTS OF THE INVENTION

It is an object of the invention to provide an approach to understanding the digestive tract, particularly to allow diagnosis of swallowing disorders, and, hopefully, to facilitate correct treatment of such disorders.

It is also an object of the invention to provide an approach to quantifying pressures applied to a bolus during a swallow, and to relating these pressures to physiological events acting on the bolus.

It is another object of the invention to provide medical equipment to facilitate the above-described approaches.

It is yet another object of the invention to provide a method for making medical equipment to facilitate the above-described approaches.

It is yet another object of the invention to provide a method for using this equipment to facilitate the above-described approaches.

It is yet another object of the invention to provide a manofluorograph having pressure data which corresponds to contemporaneous physiological events.

It is yet another object of the invention to provide a method for making such a manofluorograph.

It is yet another object of the invention to provide a method for using such a manofluorograph.

It is yet another object of the invention to provide a manofluorogram having pressure data which corresponds to contemporaneous physiological events.

It is yet another object of the invention to provide a method of making such a manofluorogram.

It is yet another object of the invention to provide a method of using such a manofluorogram.

It is still another object of the invention to improve over the limitations of the prior art to advance the diagnosis and treatment of swallowing disorders.

Other objects and advantages of the invention will become apparent from the following summary, drawings and detailed description of the invention. Although this invention is considerably broader than its application described herein, this application is used to teach a best mode and manner of practicing the invention.

OVERVIEW OF A PREFERRED EMBODIMENT

The present invention is directed to the digestive tract or a portion thereof. A preferred embodiment, useful for teaching the invention, is directed to the analysis of swallowing.

The manofluorography system generates three data forms: a four-channel strip chart recording, a manofluorograph, and a manofluorogram. The strip chart recording is a display of pressures recorded by pressure sensors in the pharynx. The manofluorograph involves the simultaneous presentation of videofluoroscopy, contemporaneous manometry data and timing information. The manofluorogram relates pressure analysis to the bolus passage. The manofluorography system therefore detects and quantifies pressure generation and its relationship to bolus transport. The manofluorographic system aids in the diagnosis and treatment of swallowing disorders by precisely characterizing a patient's swallow for analysis and comparison with other individuals.

BRIEF DESCRIPTION OF THE DRAWINGS

FIGS. 3-1, 3-2, 3-3, 3-4, 3-5, 3-6, 3-7, 3-8, 3-9 are photographs of multiple still-frames of manofluorograph videotape of a normal swallow.

FIG. 4 is a photograph of a still-frame taken from a manofluorograph videotape.

FIG. 5 is a representation of a still-frame manofluorograph.

FIG. 6 is a copy of a computer printout of pressures prior to constructing a manofluorogram.

FIG. 7 is a representation of a manofluorogram associated with a graphical representation of a throat.

FIG. 8 is a superimposition of important fluoroscopic, bolus, and manometric events on a manofluorogram of a normal swallow.

FIG. 9 is a representation of a manofluorogram of an individual with Wallenberg's syndrome with aspiration.

DETAILED DESCRIPTION OF THE INVENTION

Figure 1:
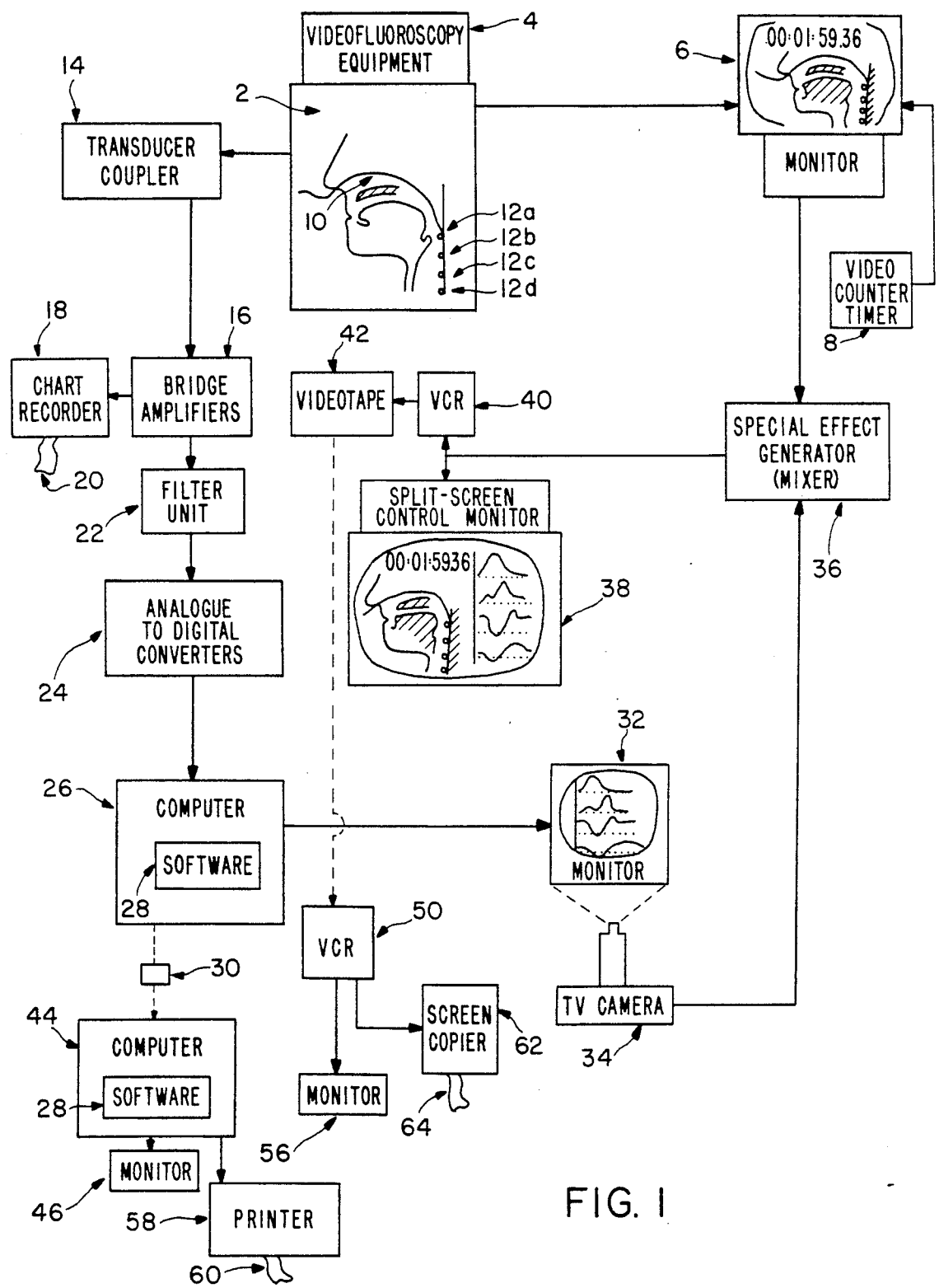
FIG. 1 is a block diagram of the invention.

FIG. 1 provides a diagrammatic overview of the equipment used to practice the present invention. Patient 2 is viewed by standard videofluoroscopy equipment 4, a General Electric Model 46-169150G82 Fluricon 300. Videofluoroscopy equipment 4 outputs a video signal to display on a GBC-MV-900 video monitor 6. Monitor 6 also shows time information from counter/timer 8, a Thalner Electronic Labs, Inc. (Ann Arbor MI) VC-436.

Catheter 10 is inserted about 20 cm through the nose and pharynx of patient 2. The nasal route allows the best position for measuring pressures generated by palate closure and the pharyngeal walls in the oropharynx. Also, the tongue motion, oral mastication, and epiglottic motion are not inhibited. The patient's head movements are not restrained as they are a compensatory factor of functional importance for many postoperative patients.

Catheter 10 is 1 meter long and marked in cm increments to identify the depth of insertion into patient 2. Catheter 10 is 3.2 mm in diameter and silicon-coated. Catheter model 16 CT/54 is available from Medical Instruments, Inc. (Hackensack, N.J.) Catheter 10 has four solid state pressure sensors 12a, 12b, 12c, and 12d with 4 cm spaces therebetween. The first sensor 12a of the solid state manometer is positioned at the tongue base; the second sensor 12b at the introitus of the larynx; the third sensor 12c at the PE segment, and the fourth sensor 12d in the cervical esophagus. Sensors 12a–d output respective signals to respective transducer couplers 14, and Medical Instruments, Inc. also supplies such couplers. Transducer couplers 14 outputs to four respective Gould Electronics (Cleveland, Ohio) model 11-4143-01 bridge amplifiers 16. The bridge amplifiers 16 output to chart recorder 18, which produces strip chart 20. Chart recorder 18 is a Bechman 4-channel plotter having a scale of −30 to 175 mm Hg with a paper speed of 5 and 10 mm per second. Strip chart 20 provides a record of swallows for a broad view of the pressure data and for quantitative checking of the pressure wave data.

Data from the bridge amplifiers 16 pass through a pole low pass Butterworth filter unit 22. Filter unit 22 sends signals from the sensors 12a–d to respective Data Translations model DT 2808 analog-to-digital converters 24, to digitize the pressure data. The Data Translation DT2808 converter is a 10-bit converter with a full-scale range of 0 to 5V. A 10-bit converter has 1,024 digitizing steps, therefore the 0 to 5 V range is divided into 4.883 mV steps. Voltage changes smaller than 4.883 mV will therefore not be visible on the subsequently described monitor. The DT2808's maximum digitizing rate is 3300 Hz composite. But for four sensors 12a–d, the maximum rate for each is 3,300/4 or 825 Hz. The Nyquist theorem governs any discrete time or sampled data system; it says that in order to faithfully digitize a signal with a band width of n Hz, sampling must be done at a rate of at least 2 n Hz. To record manometry data with frequency components up to 100 Hz, a low-pass filter with a steep cutoff is required prior to sending the data to the converters, where sampling is at a rate of at least $2 \times 100$ Hz = 200 Hz. The lowpass filter 22 is a 6-pole Butterworth design with a −3 dB point of 100 Hz. This filter attenuates at 36 dB/octave above 100 Hz. The smallest voltage that this converter can discriminate is 1/1,024 of full scale, which is −60.2 dB. The 6-pole filter will not be 60 dB down until about 270 Hz; therefore sampling should be conducted at least 270 Hz. For less critical recording, a rate of 200 Hz may be sufficient.

Converters 22 output digitized information to a Compaq Plus computer 26 equipped with an IBM CGA graphics board, 640K RAM, and an Intek 8087 "math co-processor." Data samples are read into a circular buffer in the RAM of computer 26. "Circular" means that when the buffer fills, it wraps around to the beginning and starts over, writing over old data. The buffer can hold 32,384 samples. Thus, for four sensors 12a–d, there are 32,384/4 = 8,096 samples per sensor 12. This number of samples divided by the sampling rate in Hz yields the maximum amount of data that can be stored, i.e., at 200 Hz, about 40 seconds of data can be stored.

Computer program 28 resides in computer 26, and is written in Microsoft Pascal and consists of 125K bytes of Pascal source code, plus a small amount of assembler code. Computer program 28 directs the sampling of data from convertors 24, storing the data on a disc 30, and outputting videoscreens to a monitor 32, an Amdek 12 inch data display model video 300A. Computer 26 may optionally have its own monitor, for conveniently displaying pressure data at a location where viewing will not obstruct videotaping monitor 32.

Monitor 32 is videotaped via a Panasonic model WV-1850 videocamera 34. Videocamera 34 operates in conjunction with a Panasonic model WJ-4600 C mixer/special effects generator 36. Mixer 36 also receives signals from monitor 6 to make a split screen, of which, approximately the left ⅔ is the videofluoroscopy image and timing data from monitor 6, and the right ⅓ is the manometer data from monitor 32 via videocamera 34. The split screen is displayed on GBC-ITC model MV-900 monitor 38 and recorded by a Sony U-Matic model VO-26000 video cassette recorder 40 to produce videotape 42. The combination of this videofluoroscopy with contemporaneous pressure data, preferably timing information, is a manofluorograph.

Analysis is performed on the data stored on disc 30 and by associating this data with information derived from the images on videotape 42. Disc 30 is read by a Compaq Deskpro 386 computer 44, which displays on a Compaq 386 VGA monitor 46. The computer 44 should have a 640K RAM, an Intek 80387 "math co-processor," an IBM EGA graphics board and Data Translations video boards DT 2851 and DT 2858, and a color monitor 46. Computer 44 also runs computer program 28, to compute parameters from the data from disc 30, as is more fully discussed below. Simultaneously, videotape 42 is viewed on a Sony U-Matic VO-5800 VCR 50, which has forward, reverse, and high quality still frame capabilities. Images from videotape 42 are displayed on a Sony PRM 1910 monitor 56. Timing information gathered by inspection are manually input to computer program 28 on computer 44, as is more fully discussed hereinafter.

Computer 44 is linked to a Hewlett-Packard Series II laser jet printer 58, which outputs a manofluorogram 60. Screen copier 62 is connected to VCR 50 to produce a still-frame of a manofluorogram 64.

Recording a swallow involves the patient 2 swallowing a radiopaque bolus, for example, 10 cc of liquid barium. The swallowing event is recorded on videotape 42 and reviewed on VCR 50. Videotape 42 is regulated by stopping frames, slow motion, and forward and backward image display, to associate the images with the data from disc 30. Making measurements from the images is preferably done by two observers, to serve as a check on observation validity. The manofluorograph videotape 42 can be slowmotioned, forwarded, reversed, and still-framed to analyze each event with its associated pressure generation and relation to bolus transit. The precise anatomic site of the pressure reading can be seen on each still-frame manofluorograph because sensors 12a–d are radiopaque. Based on the key events observed on the videotape 42, significant portions of the pressure data are communicated to computer program 28. Thereafter, parameters for characterizing the swallowing event are computed by computer program 28.

Figure 2:
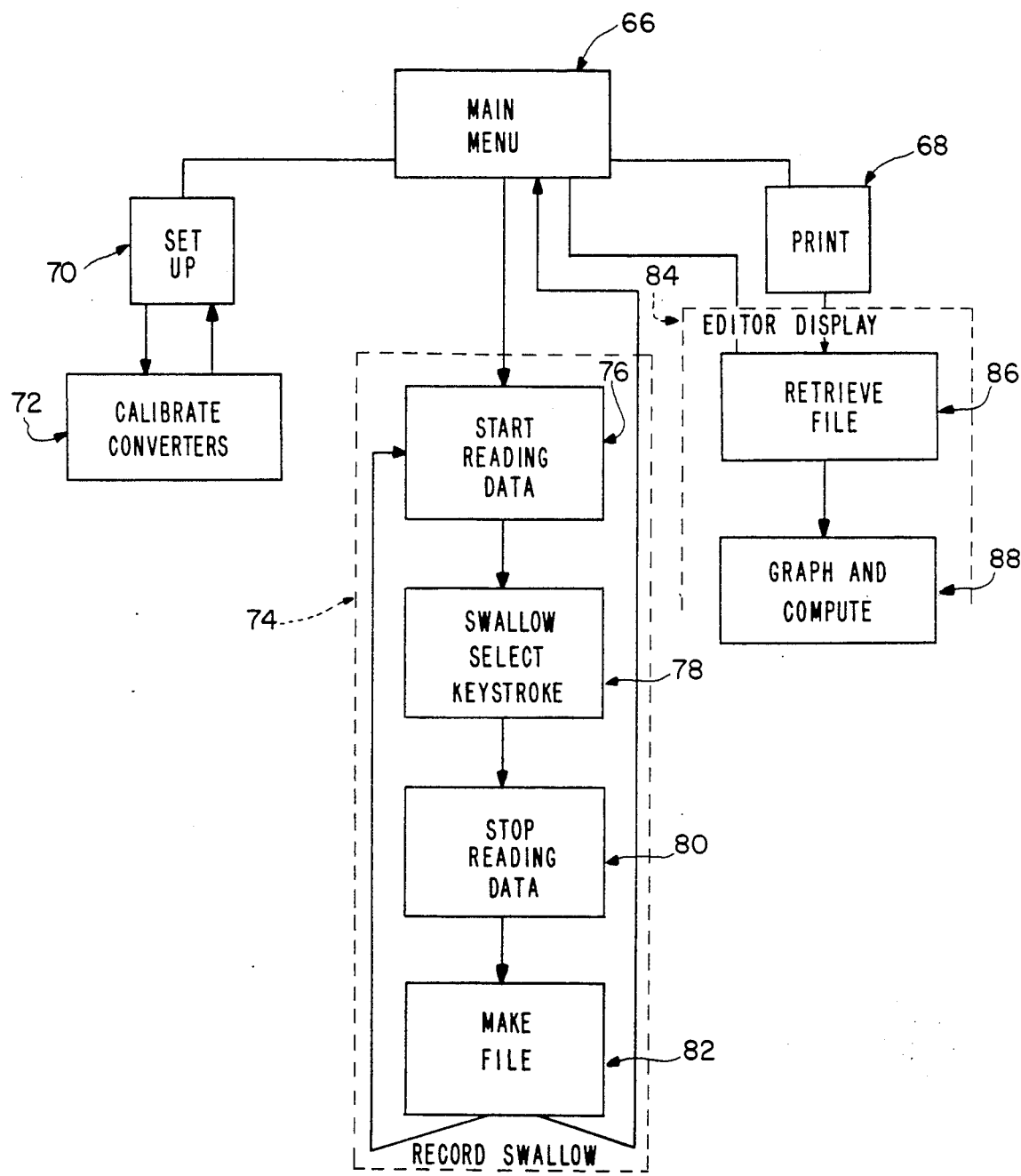
FIG. 2 is a block diagram of a computer program.

FIG. 2 shows a block diagram of the salient aspects of the first computer program 28, which was written by, and is available from, William Goolsby (Decatur, Ga.). With reference to FIG. 2, program 28 generally samples data from the converters 24 to digitize the data and displays the data in real time on the left ⅓ of monitor 38. The data is also stored in a circular buffer in computer 26. A keystroke is used to obtain a predefined amount of data, including data from before and after keystrokes. This data is stored in a file on disc 30 for later processing. Menu 66 allows access to a number of routines, including batch print 68 for making hard copy of subsequently described screens.

Set-up routine 70, also accessible from menu 66, allows entry of information about a patient and information which will control operation of the program 28. Patient information includes the patient's name and social security number. Control information includes the number of samples per second to be taken from each of the converters 24. As previously noted, for a Data Translation DT 2808 converter, the maximum sampling rate is 825 Hz, and the sampling rate should be at least two times higher than the lowpass filter cutoff frequency to ensure faithful transmission of data. Another entry to routine 70 which relates to sampling rate is the graphics refresh rate for monitor 32, which must be equal or less than the sampling rate.

Also input to set-up routine 70 are the sample times to be recorded before and after a keystroke. These sample times are in seconds, and the total time must not exceed the total time for data stored in the circular buffer.

Graphing parameters are also entered in set-up routine 70. One graphics parameter—"Trace Overlap Percentage"—adjustably allows the graphing of pressure data from one sensor to extend into the range of another sensor, to more efficiently display data in the limited screen space of monitor 32. Color controls for the display on monitor 32 are also input. Another graphics parameter is the scale limit in mm Hg for the maximum pressure. Still another such parameter sets a blank gap width for data overwriting. After data is displayed from left to right, new data is "wrapped around" to display over old data. To demarcate old and new data, a blank area or gap precedes new data that is written over old data.

Other information recorded by set-up routine 70 includes the name of the transducer, the level in cm that each which transducer has been inserted into a patient, and the filter cutoff frequency, for reference purposes. Set-up routine 70 also allows designation of the file path for storing data files. Files can be manipulated and deleted, etc. Also, a counter is used to make sequential files of a patient's swallows, which are associated with a swallow code: W (wet); D (dry); C (cookie); or B (barium). As is more fully discussed below, entering any of these letters also serves as the keystroke to trigger data recording.

Subroutine 72 of set-up routine 70 is used to calibrate converters 24. Sensors 12a–d are calibrated at body temperature (37° C.) and at two pressures. Subroutine 72 controls the display and continuous updating of raw code and voltage from the sensors 12a–d. At atmospheric pressure, to set pressure to 0 mm Hg, the gain and offset of each converter 24 is adjusted so that all sensors show the same voltage. The voltage should be a small, positive value, such as 0.30V, so that negative pressures may also be measured. Calibration is also done at a known pressure near, but less than, the full scale value for graphics display. Here, the computer finds a multiplier to compensate for any difference between the known pressure and that pressure which is reported to computer 26.

Set-up routine 70 uses the following data to identify a swallow, presented in hypothetical form below:

| Setup Information | |
| --- | --- |
| Patient Name | John Doe |
| Patient Number | 123456789 |
| Swallow Code | W |
| A/D Sampling Rate | 200.0 |
| Graphics Refresh Rate | 40.0 |
| Sample Time Before Key | 5.0 |
| Sample Time After Key | 3.0 |
| Trace Overlap Percentage | 1.00 |
| Full Scale (first, mmHg) | 200 |
| Blank Gap Width | 50 |
| Filter Cutoff Freq. | 100.0 |
| Transducer Type | Gaeltech |
| A/D Calibration Factor | 21.9037 |
| Data Directory | a: |

| -continued | |
| --- | --- |
| Setup Information | |
| mandatla | |
| Editor background color | 0 |
| Editor data curve color | 12 |
| Editor axis & text color | 15 |
| Editor int. area color | 14 |
| Editor color help | |
| Quit | |

Record swallow 74 creates a datafile of a swallow displayed on monitor 32. Block 76 starts sampling data from the converters 24 into a circular buffer in the RAM of computer 26. This data is also shown on the monitor 32 in real time. The circular buffer in RAM is under direct memory access control of computer 26.

Block 78 requires entry of a swallow code to identify the nature of a detected swallow: D (dry swallow), C (cookie swallow), B (barium swallow), or W (wet swallow) to conveniently identify what is being swallowed. Any one of these keystrokes triggers storing the prescribed data before and data after the keystroke. Typically, the protocol involves directing patient 2 to swallow. As soon as the beginning of the swallow is observed on a videofluoroscopic image, the appropriate keystroke is pressed. By gathering data prior to and after the keystroke, the operator is assured of capturing the entire swallow.

Block 80 stops the data after the sampling is complete and the buffer is full. Block 82 creates a sequential file of the data on disc 30. The disk file contains a header listing various data items, including patient name, date, time, number of samples, etc. Thereafter, the program optionally jumps to block 76, to start reading data again, or returns to the main menu 66.

Edit and Display 84 allows recalling and analyzing disk files, and is used after the program 28 is moved to reside in computer 44. Edit and Display 84 generally allows the data to be panned left and right, zoomed in and out, and performs measurements on the data. The file name, patient name, transducer level in cm, and the above-described swallow code is shown in the bottom of this screen, and pressure data from each of the sensors 12a–d is graphed on the monitor 46 by graph and compute block 88. Time, in seconds of recorded data, forms the X-axis and pressure in mm Hg forms the Y-axis for each trace.

A crosshair cursor is operated by the arrows on the keypad of computer 44 or a mouse. At all times, the cursor's current position in absolute and relative coordinates is shown at the top of the screen. The four coordinate numbers are "absolute X, absolute Y, relative X, relative Y". Absolute coordinates correspond to the X and Y axis scales. Relative coordinates correspond to the X and Y zero points set by the last "Anchor" command, as is further described below. Both absolute and relative coordinates are keyed to one of the four data traces, shown by "T" and a digit in the upper left corner of the screen. Again it is noted that a "trace" refers to a graph of pressure data from one sensor 12. The T command sets which trace will be associated with the cursor. Traces are numbered 0 through 3, with 0 being the top trace. The cursor may be moved 10 times faster by pressing shift simultaneously with arrows.

Block 88 has the following significant functions:

```
F1/F2 or F9/F10 - Move data left/right ⅛ screen
F3/F4 or F5/F7 - Expand/compress X scale by 2
F8 - (followed by A or B) draw arrow marker
L/R Arrows - Crosshair cursor left/right (shift-faster)
U/D Arrows - Crosshair cursor up/down (shift-faster)
A - Drop Anchor (set relative X/Y to 0)
B - Batch print command menu
I - Integrate area under trace (unitary mode only)
M - Go to Multiple trace mode
N - N- = previous .Rxx file, N+ = next .Rxx file
P - Print current screen
Q - Quit Editor
S - Store data back to disk
Tn - Make relative X/Y corr. to trace n (0-3)
Un - Go to Unitary mode for trace n (0-3)
Z - Define X Zero at current crosshair position
Alt-p, Alt-d, Alt-1 - Save rel. pressure, rel. duration,
    integral
? - This help screen
```

The function keys adjust the portion and scale of the image displayed on monitor 46, except for "F8" which sets a marker for printing an annotation.

Anchor—The A command—sets an Anchor at the current cursor position. This resets the relative X,Y cursor readout to 0,0, but the absolute X,Y readout is unaffected. By "dropping an Anchor," the computer is directed first to define relative time and pressure as 0, such that by changing position of the cursor one is allowed to measure the relative change(s) in time and (or) pressure. Computer program 28 has access to pressure data from the sensors 12a-d, and based on the data sampling rate, time is determined, at least preliminarily.

Redefine X zero - Zero time in X may be redefined at any point by moving the cursor to the desired point and pressing the Z keystroke. The X axis and cursor readouts will be updated to reflect the new zero time. The data file on disk will not be altered by this command, unless it is followed with an "S" keystroke, which restores the file. Restore file—The S command, as previously mentioned, will re-store the data to the same file name. This is only useful to update a new value of time-zero; no other parameters of the file will be altered.

In order to drop the Anchor with precision, program 28 uses the T (trace) and U (unitary mode) commands.

Trace—the T command, followed by a digit in the range of 0-3, designates which of the four data traces is linked to the cursor readout. That is, at any given time, the cursor readouts refer to only one of the traces. The trace currently in effect is shown by "T" and a digit in the upper left corner of the screen.

Unary mode—the U command, followed by a digit in the range 0-3, will clear the screen and redraw only the single trace specified. This gives more resolution so that finer details can be observed. Pan, zoom, cursor movement and all other commands operate as usual in Unary mode, except that only one trace is displayed. The editor must be in Unary mode before doing an integration, as is more fully described below.

Multiple trace mode—the M command returns from Unary mode to the normal 4-trace mode. First, the manofluorogram 98 is panned to locate the ⅛ of a screen of interest on monitor 46. To drop an Anchor from the Multiple trace mode, "U" and a number in the range of 0-3 is entered to show an expanded presentation of data from one sensor. "T" and a number is entered to identify which sensor is limited to the Anchor.

Integrate—The I command, commences an integration operation. In the Unary mode, press "I" once, move the cursor to the X,Y coordinate of the start of integration and press "I" again; move the cursor to the X end point and press "I" a third time. The program will measure the area under the data trace and highlight that area. When done, the bottom line displays the result in units of mmHg×seconds.

Integration takes all the area under the curve down to the Y coordinate of the start cursor. It is not necessary to integrate down to 0 mmHg. The Y coordinate of the end cursor is ignored; i.e., the Y baseline is always a straight horizontal line extending across from the start Y position. Areas of negative pressure are also integrated. That is, if the curve falls below the Y baseline, the integrated area will be negative for this portion of the curve.

In view of the number of screens that may be of interest, the previously mentioned batch print 68 is preferable over printing screen by screen.

File commands include "N" which calls up the next or previous file, depending on whether a "+" or a "-" is thereafter depressed. The Alt-p, Alt-d, and Alt-1 functions store observed pressure, duration and integral values in a cumulative file of data from other patients. Quit ends graph and compute 88 and returns to menu 66.

Figures 1, 3:
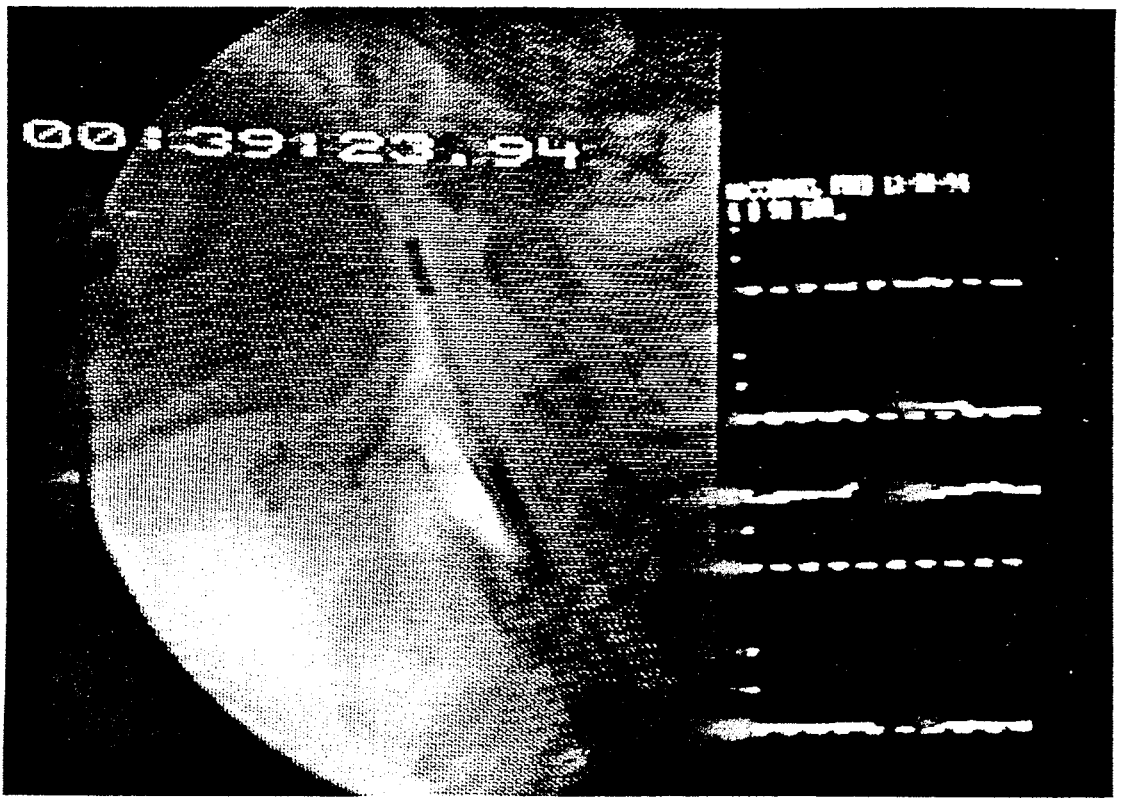
Figures 2, 3:
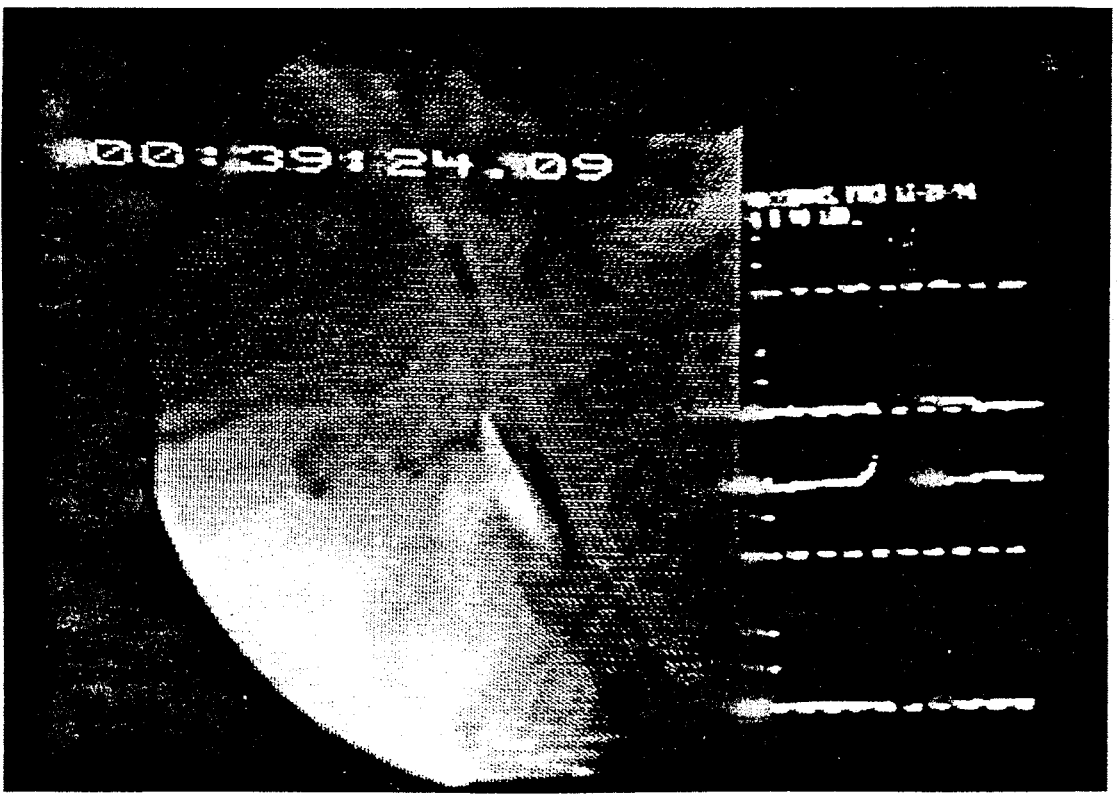
Figure 3:
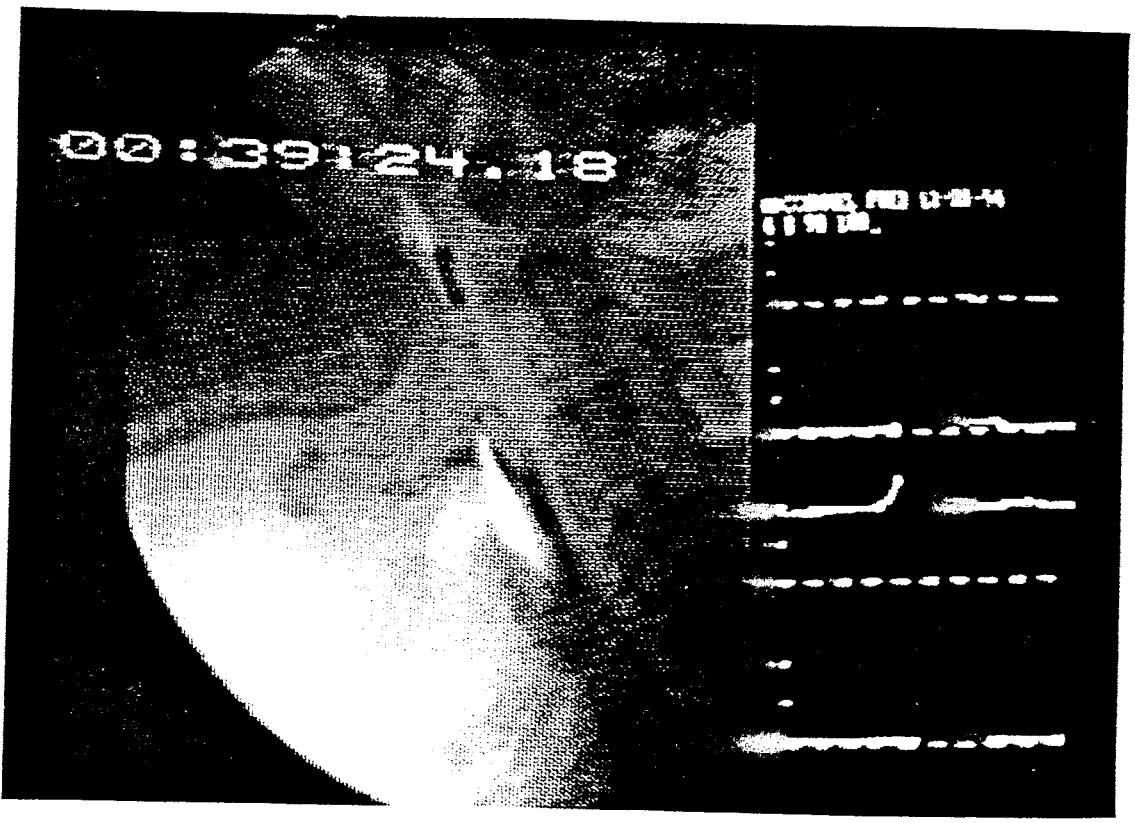
Figures 3, 4:
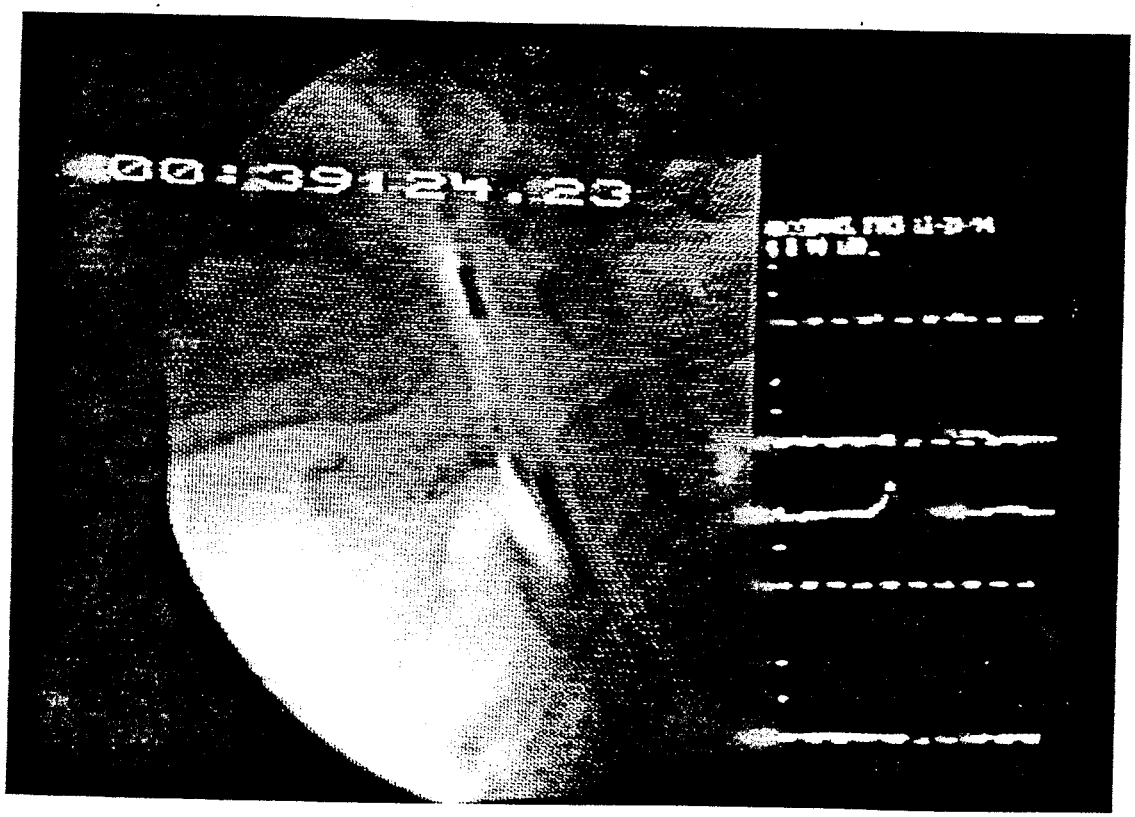

As previously suggested, the manofluorography system involves viewing a series of still frames from a manofluorograph of a swallow. FIGS. 3-1, 3-2, 3-3, 3-4, 3-5, 3-6, 3-7, 3-8, 3-9 exemplify a manofluorograph, but showing a photograph of multiple still-frames of a manofluorograph from videotape corresponding to videotape 42 in FIG. 1. FIGS. 3-1, 3-2, 3-3, 3-4, 3-5, 3-6, 3-7, 3-8, 3-9 show still-frames of a normal swallow. FIG. 4 is a photographic enlargement of a still-frame from a videotape of a manofluorograph. Although FIGS. 3-1, 3-2, 3-3, 3-4, 3-5, 3-6, 3-7, 3-8, 3-9 and 4 are of a videotape, a manofluorograph may be fixed in other media, such as digitized video image information.

Figures 3, 4, 5:
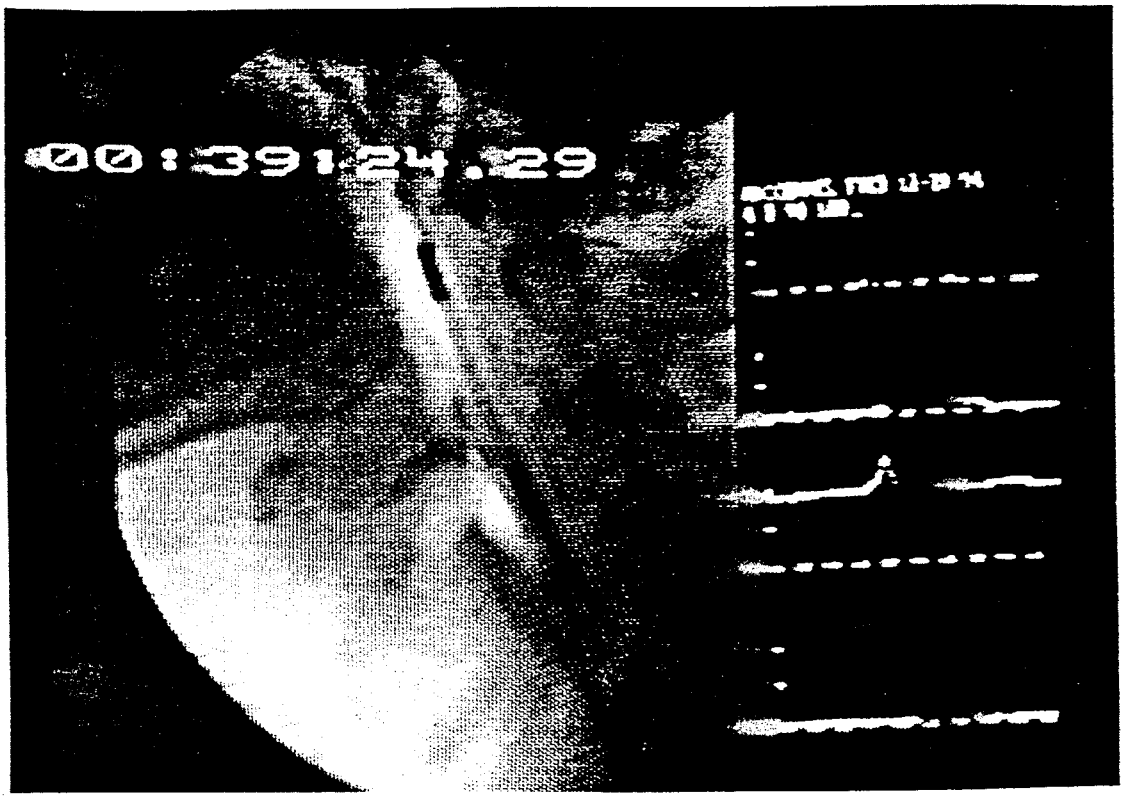

A representative still-frame manofluorograph with identifying information superimposed thereon is presented in FIG. 5. The manofluorograph in FIG. 5 includes the combination of videofluoroscopy portion 90 and a manometry portion 92. In FIG. 5, superimposed on videofluoroscopy portion 90 is the time of the image shown in hours, minutes, seconds, and 1/100 ths of a second, as generated by counter/timer 8. In the still-frame manofluorograph of FIG. 5, the bolus 94 is distinguishable from tongue 96, hyoid bone 98 and larynx 100. Sensors 12a, b, c, and d are also visible. These sensors 12a-d provide corresponding data on the manometry portion 92 of the still-frame manofluorograph. The still-frame manofluorograph in FIG. 5 also shows pressure data for each sensor 12. Real-time is recorded on the X axis, and absolute pressure is recorded along the Y axis, allowing the passage of the bolus head and tail by a manometry site to be identified from a sequence of manofluorographs such as that in FIG. 5. Significant events are manually identified and computations are performed by computer program 28, as previously described.

Figures 3, 4, 5, 6:
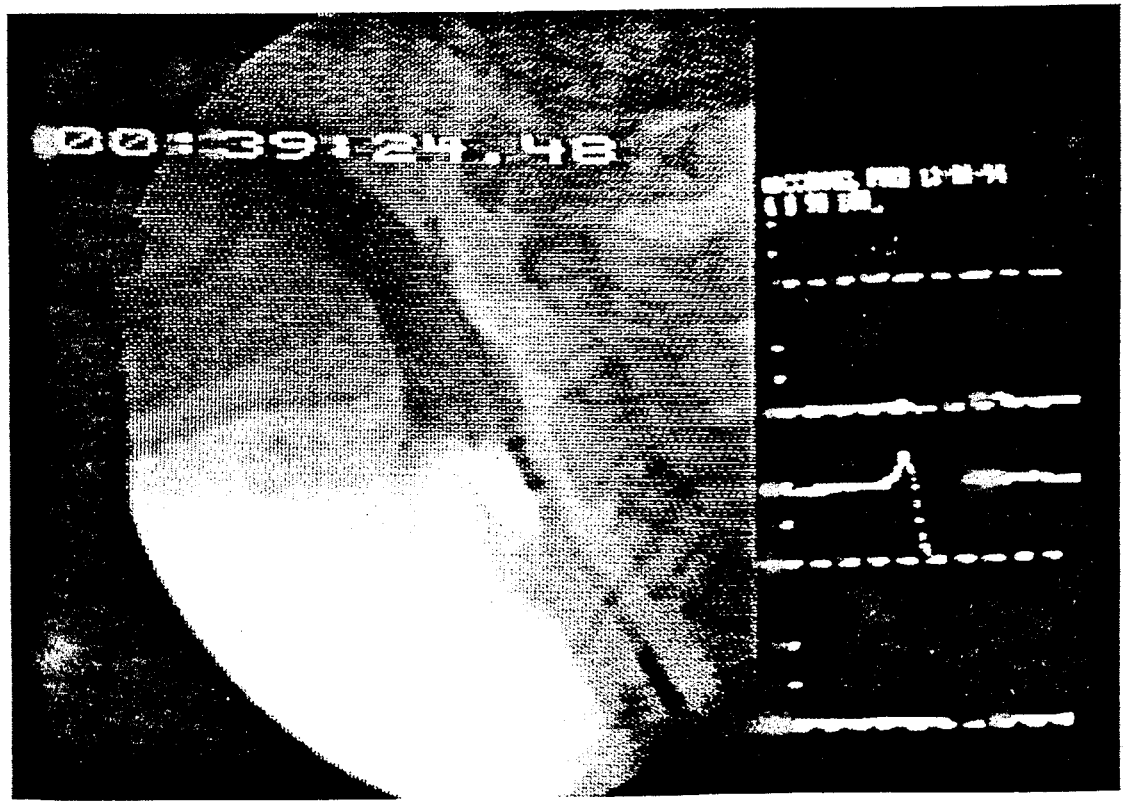
Figures 3, 4, 5, 6, 7:

FIG. 6 is a computer printout of pressures prior to constructing a manofluorogram. It is provided in contrast to FIG. 7 and includes a manofluorogram of a normal swallow with identifying information superimposed thereon, and shown in association with a graphical representation of a throat. The passage of the bolus is shown at each level of the sensors 12a-d, respectively. In FIG. 7, points marked by the letter "A" mark the time of arrival of the bolus head at each manometry site, and points marked "B" mark the passage of the bolus tail by the manometry site. These are identified to computer program 28 by dropping an Anchor. For fluoroscopic framing of the pharynx, only the first three sensors are shown.

The manofluorograph system involves means for determining quantitative parameters, which are reflected in FIG. 7.

PHARYNGEAL TRANSIT TIME

Pharyngeal transit time is defined herein as the time the bolus takes to pass over the approximately 8 cm distance from the oropharynx to the PE segment. It is not precisely 8 cm, due to the movement of the catheter. However, the present invention uses the sensors 12 to define the transit time. Pharyngeal transit time is measured from the moment that the bolus head touches the first radiopaque sensor 12a in the oropharynx until the time that the bolus tail leaves the sensor 12c in the PE segment.

By using the sensor 12b, spaced 4-cm between 12a and 12c, two additional pharyngeal transit times can be measured. Each of these "segmental pharyngeal transit times" is influenced by a different driving force, indicating the efficiency of each force, as is more fully described below.

OROPHARYNGEAL TRANSIT TIME

This is the time that the bolus takes to pass from sensor 12a to sensor 12b, i.e., from between the tongue base to the level of the laryngeal introitus.

HYPOPHARYNGEAL TRANSIT TIME

This is the time that the bolus takes to pass the approximately 4-cm distance between the level of the laryngeal entrance at sensor 12b to the level of the cricopharyngeal muscle (CPM) at sensor 12c. Again, it is noted that measurements herein are computed from sensor to sensor regardless of catheter movement.

AVERAGE PHARYNGEAL BOLUS VELOCITY

This value is based on the pharyngeal transit time divided by the 8-cm distance between sensors 12a and 12c.

OROPHARYNGEAL BOLUS HEAD VELOCITY

This is the velocity of bolus head over the 4-cm distance between the sensor 12a in the oropharynx and the sensor 12b at the level of the laryngeal entrance. This parameter is dependent on the force applied to the bolus by the pharyngeal walls and the tongue driving force.

HYPOPHARYNGEAL BOLUS HEAD VELOCITY

This is the velocity of the bolus head over the 4-cm distance from the sensor 12b, at the level of the laryngeal entrance, and the sensor 12c, at the cricopharyngeal muscle. This parameter is dependent on the forces applied to the bolus by the "oropharyngeal propulsive pump" and the hypopharyngeal suction pump.

TONGUE DRIVING FORCE (TDF)

This is a measure of the pressure produced by the tongue applied directly onto the bolus tail in the oropharynx, measured at sensor 12a. The change in pressure over time is calculated by computer program 28. This integral is the area of the pressure measured during the time of bolus transit, between points A and B in FIG. 7, recorded at the level of oropharyngeal sensor 12a. Momentum units mu (mm Hg×s) are used.

TRANSMITTED TONGUE DRIVING FORCE (TTDF)

The transmitted tongue driving force (TTDF) is measured at the level of the laryngeal introitus above the arytenoid level. This is the tongue driving force transmitted by means of the bolus. This value is an integral of pressure that is applied to the bolus from the tongue above. Since the TTDF is dependent on the size of the bolus-containing space, an impairment of PE segment opening can cause an increase in the TTDF because bolus outflow is impaired. Decreased TTDF is due to a decreased tongue driving force.

PHARYNGEAL CLEARING FORCE (PCF)

This force is the pharyngeal constrictor pressure that is applied to the bolus as measured at the level of the laryngeal introitus. This is determined by identifying the passage of the bolus during the observed pharyngeal contraction. This value is an integral of pressure that is applied to the bolus.

OROPHARYNGEAL PROPULSION PUMP FORCE (OPPF)

This force is measured at the level of the laryngeal introitus. It consists of the two previously discussed forces TTDF and PCF. At this level, the sensor 12b is out of direct reach of the tongue base. The pressure recorded represents the tongue driving pressure in contact with the oropharyngeal walls and is applied to the bolus. This parameter is affected by both functional regions of the pharynx (oropharynx, hypopharynx). A low OPPF indicates a small resistance to bolus flow in the hypopharynx and/or a low tongue driving force generated in the oropharynx, and a high OPPF represents the greater resistance to bolus flow in the hypopharynx and/or a greater tongue driving force generated in the oropharynx. The numerical value is calculated by computer program 28 as an integral by the area of the pressure measured during the time of bolus transit, between points A and B in FIG. 7, recorded at the level of the laryngeal introitus. The OPPF consists of the TDF and the PCF. Momentum units are also used for OPPF.

HYPOPHARYNGEAL SUCTION PUMP FORCE (HSPF)

A negative pressure is measured during swallowing in the postcricoid segment at the level of the CPM and sensor 12c. Negative pressure times time is graphed over the course of time. The computer program 28 computes the integral from the surface between the negative pressure wave pattern and the 0 mm Hg baseline. This measurement begins when the bolus head contacts sensor 12c and ends when pressure reaches 0. These parameters are of two types: the pressure parameters are an index of the forces applied to the bolus and the remaining parameters measure speed of bolus transit. The asymmetry of pressure generation of the PE segment does not appear to be significant in determining this parameter. The pressure is measured only during the time the bolus passes the manometric site. The liquid of the bolus equalizes the pressure generation of the segment.

The hypopharyngeal suction pressure determination also reduces error from motion of the manometric site in the PE segment. The negative pressure is generated in a cavity developed by laryngeal elevation. The cephalic aspect of this cavity is the bolus head. If a sensor is in a cavity, it will not reflect asymmetrical pressures. A positive pressure can be generated by a force applied directly to the manometer or in a cavity. A negative pressure can be measured only in a cavity.

The resting pressure measured in the PE segment is due to pressure applied directly to the manometry site by the pharyngeal walls. It is not as significant to swallowing because of the negative pressure generated somewhat later. The length of the segment with elevated resting pressure is approximately 2 cm so that the catheter can move out of the high-pressure zone during swallowing. However, since the negative pressure is a cavity pressure, it is not affected by catheter movement. The negative pressure is of greater functional significance because it is as a result of the development of this pressure that the bolus flows through the PE segment.

Using the manofluorography system also involves relating quantitative parameters to physiology. Pressure generation in the pharynx can be divided into two functional regions—the oropharynx and the PE segment in the hypopharynx. In the oropharynx, a propulsive bolus force is generated by the tongue and the pharyngeal walls. Conceptually, the pressure generation mechanism can best be understood as a pump. The tongue acts as a piston, and the pharyngeal walls are the chamber of the pump. With closure of the larynx and the nasopharynx, a closed chamber is created. The tongue base delivers the bolus and then compresses the closed, bolus-filled chamber. The tongue driving pressure is an index of the tongue force applied to the bolus in the oropharynx.

A decrease in tongue driving pressure corresponds to a number of different types of dysphagia. A pathologic condition that decreases tongue mobility, such as surgical resection, cranial nerve XII paralysis, neuromuscular disorders, or degenerative neurologic diseases, will decrease the transmitted tongue driving force. Chamber defects can occur with palate resection, pharyngeal wall resection, or paralysis. Another example of a chamber defect is the decreased tongue driving force in oropharyngeal muscular dystrophy. In this genetic muscular dystrophy, there is paralysis of the constrictor muscles that results in an adynamic pharyngeal chamber.

With a decreased tongue driving force, the oropharyngeal bolus velocity will decrease, and the oropharyngeal transit time will increase. The tongue driving pressure can increase by voluntary or involuntary compensation. When there is obstruction to bolus flow in the lower pharynx, tongue driving force will increase to overcome the obstruction. This is one way the swallowing therapist can help the patient compensate for a dysphagia. With laryngeal elevation, the tongue base can be held in a prolonged posterior position against the posterior wall to drive a bolus down the pharynx. The voluntary practice of this maneuver is termed the "Mendelsohn maneuver." A person can keep a prolonged, increased tongue driving pressure by voluntarily keeping the tongue base against the posterior wall.

Pharyngeal clearing force is the pressure applied to the bolus by the pharyngeal constrictor sequential contraction measured at the level of the laryngeal introitus above the arytenoids. If there is paralysis of the constrictor muscles or a pharyngeal wall resection, a decreased or zero pharyngeal clearing force will be measured. With the absence of pharyngeal clearing force, there will be bolus residue that remains after bolus passage. Upon reopening of the larynx after bolus passage, the residual bolus will be aspirated.

The absence of the constrictor contraction does not lead to failure of bolus passage. This finding is in contrast to the theory of those who advocate that bolus passage is due to pharyngeal peristalsis down the pharyngeal wall. In our studies with liquid barium, the tongue is the major driving force. With more solid material, the pharyngeal clearing pressure may become more important.

The oropharyngeal propulsive pump (OPPF) is the pressure measured at the laryngeal introitus. Changes in this value are an important indicator of dysfunction. For example, a patient may feel that there is something wrong in the throat, but a barium swallow and even standard manometry results may be normal. However, an elevated OPP can be identified. When PE segment opening is impaired, there is an increased propulsive pressure applied to the bolus from the oropharynx, in a manner analogous to an increase in output pressure when a pump is pushing against an obstruction. If the pump is defective, with a malfunction of the piston or chamber, then a decreased output pressure will be measured. Thus, if the tongue driving force or the pharyngeal clearing force are impaired, a decreased oropharyngeal propulsive pump force is measured.

The "hypopharyngeal suction pump" is the phrase used to characterize the negative pressure generated in the hypopharynx. This phrase is used instead of the "PE segment" because the negative pressure is measured in an area wider than the PE segment. During swallowing, a negative (cavity) pressure is generated by laryngeal elevation away from the posterior wall. At the time of the elevation, the space is closed by the bolus above and the esophagus below.

Normal flow of the bolus depends on the development of this negative pressure. If less negative pressure is generated, there will be an increase in the hypopharyngeal transit time and a decrease in the hypopharyngeal velocity. There may also be a compensatory increase in the tongue driving force that will result in an increased oropharyngeal propulsive force. In cases in which there is no propulsive force developed by the oropharyngeal propulsive pump, swallowing can still be accomplished if a negative pressure is developed. In some patients, this may be the only effective pressure generator for swallowing. If there is no negative pressure or positive oropharyngeal propulsive force, effective swallowing cannot occur, and a gastrostomy will be required.

Using the manofluorography system further involves relating quantitative parameters to physiological events. Table 1 displays the timing of the fluoroscopic, bolus, and manometric events in a normal swallow. The standard deviation ("SD") of

TABLE 1

Timing of Fluoroscopic, Bolus, and Manometric Events

| | Mean +/− SD | Relative Variance |
|---|---|---|
| Fluoroscopic Events | | |
| 1. Onset of hyoid bone superior motion | 0.000 | ... |
| 2. Occurrence of first tongue touch | 0.285 +/− 0.089 | 0.31 |
| 3. Onset of anterior hyoid tone and tongue motion | 0.524 +/− 0.143 | 0.27 |
| 4. Epiglottis horizontally downfolded | 0.761 +/− 0.151 | 0.19 |
| 5. Hyoid bone in most anterior position | 0.858 +/− 0.182 | 0.21 |
| 6. Epiglottis completely downfolded | 0.896 +/− 0.173 | 0.19 |
| 7. Onset of hyoid bone inferoposterior drop | 1.277 +/− 0.165 | 0.13 |
| 8. Onset of linguopharyngeal detachment with refolding of epiglottis | 1.326 +/− 0.204 | 0.15 |
| 9. End of inferoposterior and onset of posteroinferior hyoid bone drop | 1.501 +/− 0.245 | 0.16 |
| 10. Epiglottis back in resting position | 1.513 +/− 0.220 | 0.14 |
| 11. Hyoid bone back in resting position | 1.955 +/− 0.403 | 0.20 |
| Bolus Events | | |
| 12. First contact of bolus head with first sensor | 0.656 +/− 0.141 | 0.21 |
| 13. First contact of bolus head with second sensor | 0.749 +/− 0.144 | 0.19 |
| 14. First contact of bolus head with third sensor | 0.849 +/− 0.142 | 0.16 |
| 15. Last contact of bolus tail with first sensor | 0.852 +/− 0.156 | 0.14 |
| 16. Last contact of bolus tail with second sensor | 1.211 +/− 0.172 | 0.14 |
| 17. Last contact of bolus tail with third sensor | 1.385 +/− 0.145 | 0.09 |
| Manometric Events | | |
| 18. Onset of E wave | 0.259 +/− 0.121 | 0.43 |
| 19. Peak of E wave | 0.488 +/− 0.121 | 0.23 |
| 20. Slow onset of T wave | 0.708 +/− 0.150 | 0.21 |
| 21. 0 mmHg at CMP level | 0.747 +/− 0.154 | 0.20 |
| 22. Sharp increase in T wave | 0.852 +/− 0.158 | 0.18 |
| 23. Most negative pressure of CPM level | 0.900 +/− 0.180 | 0.20 |
| 24. Peak of T wave | 1.072 +/− 0.150 | 0.13 |
| 25. Slow onset of C wave in second lead | 1.099 +/− 0.170 | 0.15 |
| 26. Sharp increase of C wave in second lead | 1.211 +/− 0.177 | 0.14 |
| 27. Peak of C ave in second lead | 1.340 +/− 0.192 | 0.14 |
| 28. End of T wave | 1.390 +/− 0.169 | 0.12 |
| 29. End of C wave in second lead | 1.492 +/− 0.244 | 0.16 |
| 30. Onset of C wave in third lead | 1.494 +/− 0.242 | 0.15 |
| 31. End of C wave in third lead | 3.258 +/− 0.334 | 0.10 |

The data from Table 1 have been combined to form Table 2, to relate fluoroscopic, manometric and bolus transport events in time.

TABLE 2

Relationships of the Events in Time

| Time, ms | Fluoroscopic Events (Lateral View) | Manometric Events | Bolus Events |
|---|---|---|---|
| 000–100 | (000) Onset of hyoid bone and tongue base motion superiority | | (000) No bolus motion in oral cavity |
| 100–200 | | | |
| 200–300 | (259) Laryngeal elevation onset (285) Tongue base touches pharyngeal wall | (259) E (elevation wave onset in PE* segment | |
| 300–400 | | | |
| 400–500 | | (488) Peak of E wave in PE segment | |
| 500–600 | (524) Hyoid bone and tongue base anterior motion with opening of oropharynx for bolus | | (524) Onset of bolus entering oropharynx |
| 600–700 | | | (656) Bolus head at first sensor (oropharnyx) |
| 700–800 | (708) Tongue base clears bolus oropharynx | (708) T (tongue) wave onset in oropharynx (747) 0 mm Hg at PE segment | (749) Bolus head at second sensor (laryngeal introitus) |
| | (761) Epiglottis horizontal in pharynx | | |
| 800–900 | | | (849) Bolus head at third sensor (mid PE segment) |
| | (852) Tongue base compresses against pharyngeal walls and | (852) Sharp increase of T wave | (852) Bolus tail leaves first sensor |

TABLE 2-continued

Relationships of the Events in Time

| Time, ms | Fluoroscopic Events (Lateral View) | Manometric Events | Bolus Events |
|---|---|---|---|
| | empty lumen | | |
| | (858) Hyoid bone in anterior position | | |
| | (896) Epiglottis downfolded above arytenoids | | |
| 900–1000 | | (900) Maximum negative pressure at PE segment | |
| 1000–1100 | | (1.072) Peak of T-wave amplitude | |
| | (1.099) Pharyngeal walls clear bolus tail from laryngeal introitus | (1.099) C (pharyngeal contraction) wave onset at larngeal introitus | |
| 1100–1200 | | | |
| 1200–1300 | | (1.211) Sharp increase of C wave at second sensor (laryngeal introitus) | (1.211) Bolus tail leaves second sensor (laryngeal introitus) |
| | (1.277) Onset of hyoid bone descent | | |
| 1300–1400 | (1.326) Onset of laryngeal descent | | |
| | | (1.340) Peak of C-wave amplitude at laryngeal introitus | |
| | (1.390) Onset of orophryngeal reopening and upward unfolding of epiglottis | (1.390) End of T wave | (1.385) Bolus tail leaves third sensor (mid PE segment) Entire bolus in esophagus |
| 1400–1500 | | (1.492) End of C wave at laryngeal introitus | |
| | | (1.494) Onset of C wave at mid PE segment | |
| 1500–1600 | (1.501) (onset of posteroinferior drop of hyoid bone | | |
| | (1.513) Epiglottis returns to resting position | | |

*Pe indicates pharyngoesophageal.

Figures 3, 4, 5, 6, 7, 8:
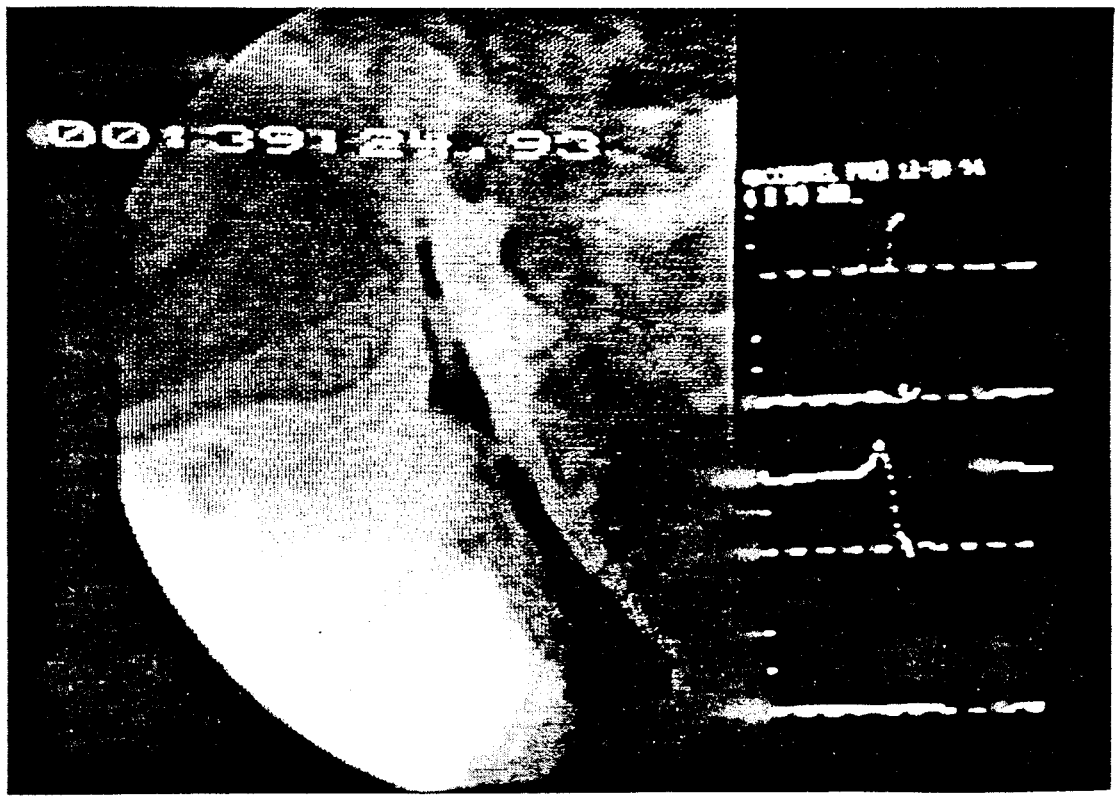

The events, numbered in Table 1, are shown in FIG. 8 superimposed on a manofluorogram. In FIG. 8, fluoroscopic events are shown in numbered circles 1–11; bolus events are shown in numbered triangles 12–17 and manometric events are shown in numbered rectangles 18–31. Note that to preserve the sequence of events from Table 1, the numbering system in FIG. 8 does not correspond to numbers used elsewhere herein.

The resting PE segment pressure is generated by the muscular constrictor tone of the surrounding structures. Before the swallow, the pressure sensor 12c shows a resting pressure of about 45 mm Hg. It can be measured in the hypopharynx behind the lower aspect of the arytenoids extending downward to 1 cm below the cricoid (PE segment). This PE segment pressure is asymmetric, with the highest pressure recorded in the anteroposterior dimension.

The onset of hyoid bone motion (No. 1, FIG. 8) is used as the zero point for the start of the pharyngeal swallow. This event is chosen because hyoid bone motion is of importance in the preparation and execution of the pharyngeal swallow.

The first swallowing pressure event is the E wave, recorded in the PE segment. (No. 18, FIG. 8) indicates its beginning. This pressure wave is superimposed on the resting pressure. The E wave occurs at about 0.259 s (No. 18, FIG. 8) after the onset of the hyoid bone elevation. A large standard deviation shows that different subjects vary greatly in the time spent on the preparatory tongue motion. The peak of the E-wave amplitude occurs at 0.488 s (No. 19, FIG. 8).

The onset of the E wave occurs first at the lower level of the cricoid and becomes progressively later upward toward the arytenoids.

The fall of the resting pressure occurs as a continuation of the decline of the E wave pressure. On the fluoroscopy, the decline in the PE segment resting pressure coincides with the anterior motion of the hyoid bone (No. 3, FIG. 8). As shown in Table 1, the onset is at about 0.524 s. This motion of the hyoid bone draws the larynx superiorly and anteriorly under the tongue base. The bolus starts to move from the oral cavity at the beginning of the decline of the resting pressure. The tongue base moves the bolus into the valleculae and the superior hypopharynx. This was opened by the hyoid bone pulling the tongue base and the larynx anteriorly. The cricopharyngeal muscle relaxes during elevation, which also opens the PE segment. Both laryngeal elevation and cricopharyngeal relaxation are essential for normal opening of the PE segment for bolus passage.

The relaxation of the cricopharyngeal muscle can lower the resting pressure to zero. Immediately before the arrival of the bolus, however, a negative (subatmospheric) pressure begins to be generated in the PE segment (No. 21, FIG. 8). This negative pressure is generated during laryngeal elevation. A negative PE segment pressure of up to −30 mm Hg can be recorded during dry swallow. The negative pressure reaches a maximum at 0.900 s (No. 23, FIG. 8). The bolus head reaches the postcricoid segment 50 ms earlier (No. 14, FIG. 8) (0.849 s).

After the peak of the E wave at about 0.488 s (No. 19, FIG. 8) and the onset of its decline in the PE segment, a pressure is generated in the oropharynx that is termed the T wave (No. 20, FIG. 8) which has an onset at about 0.708 s. The bolus head has reached the level of the laryngeal introitus at about 0.749 s (No. 13, FIG. 8). At the time of the T wave onset, the oropharynx is a closed cavity with the nasopharynx and the PE segment being closed. The T wave is a pressure wave produced by the tongue base moving posteriorly. This reduces the size of this closed cavity. With the decreasing volume of the closed oropharyngeal cavity, an increased pressure is recorded simultaneously in all the manometric leads in the cavity. The cavity is filled with the bolus that is being cleared by the tongue base. On opening of the PE segment, with the bolus leaving the oropharynx, a small notch is recorded in the T wave. This notch is termed a "flow notch" because it is produced by the flow of the bolus from the oropharynx (No. 22, FIG. 8) at about 0.852 s. After the flow notch, no bolus is present at the oropharyngeal manometric sensor (No. 13, FIG. 8).

The pressure measured after the notch is produced by the tongue force against the oropharyngeal walls. The major peak of the T wave begins after the tongue has cleared the bolus tail distally. The tongue base continues posteriorly, pressing against the palate and pharyngeal walls. The T wave pressure, secondary to this compression, reaches peak amplitude at 1.072 s (No. 24, FIG. 8). After the maximum amplitude of the T wave (No. 24, FIG. 8), another peak is recorded (FIG. 8, No. 24A). This peak coincides on fluoroscopy with the contraction of the oropharyngeal walls. This pressure is generated by the contraction of the superior pharyngeal constrictor and occurs about 0.280 s after the bolus tail has left the oropharyngeal sensor. With this time sequence, the tongue is the main driving force of the bolus because the pressure from the pharyngeal constrictors occurs after the bolus tail has passed. The T wave amplitude subsides when the tongue moves away from the pharyngeal walls and ends at 1.390 s (No. 28, FIG. 8).

The major pressure wave at the level of the laryngeal introitus is the C wave. It begins at about 1.099 s (No. 25, FIG. 8), approximately 0.4 s after the onset of the T wave. Between Nos. 25 and 26 (FIG. 8), the force of the pharyngeal contraction eliminates the bolus from the level of the laryngeal introitus. This pressure is applied onto the tail of the bolus and is considered to be a bolus-clearing pressure. The bolus leaves the second sensor at about 1.211 s (No. 26, FIG. 8). (No. 16, FIG. 8) The rest of the C wave is applied onto the empty pharyngeal lumen.

In the PE segment, the onset of the C wave (No. 30, FIG. 8) at 1.494 s pressure ends the relation period. It occurs approximately 0.100 s after the bolus tail has left the third sensor (No. 17, FIG. 8) at about 1.385 s.

CASE PRESENTATIONS

Case 1

Figures 3, 4, 5, 6, 7, 8, 9:
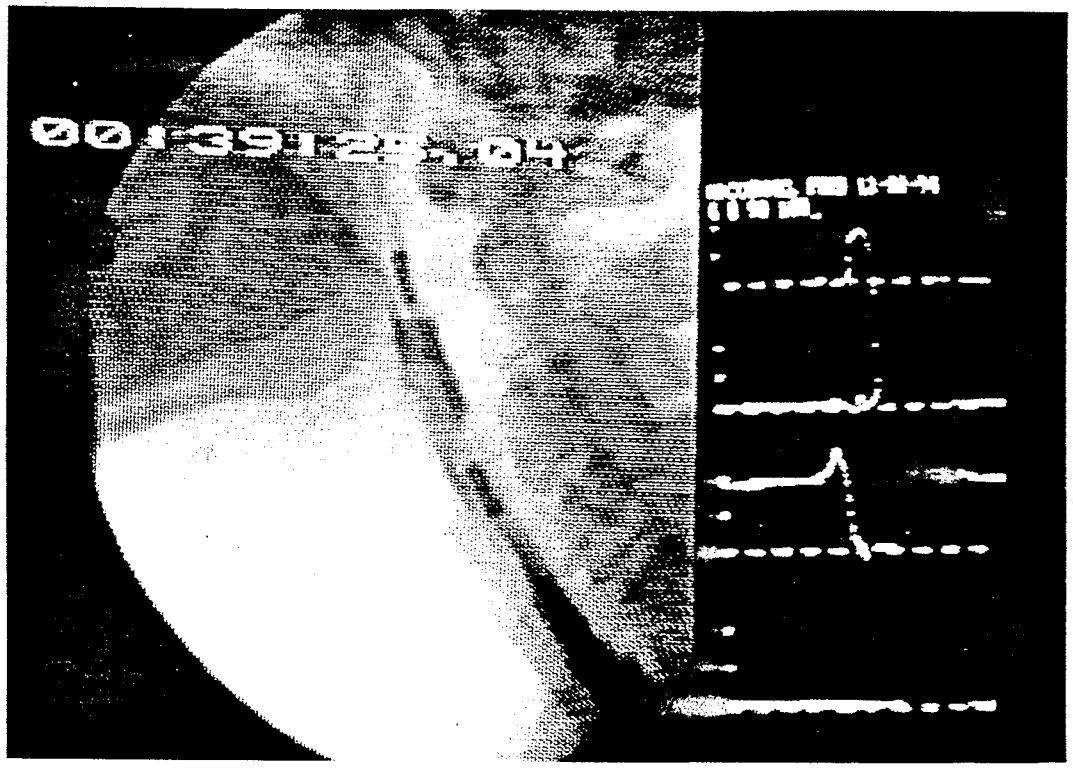
Figure 5:
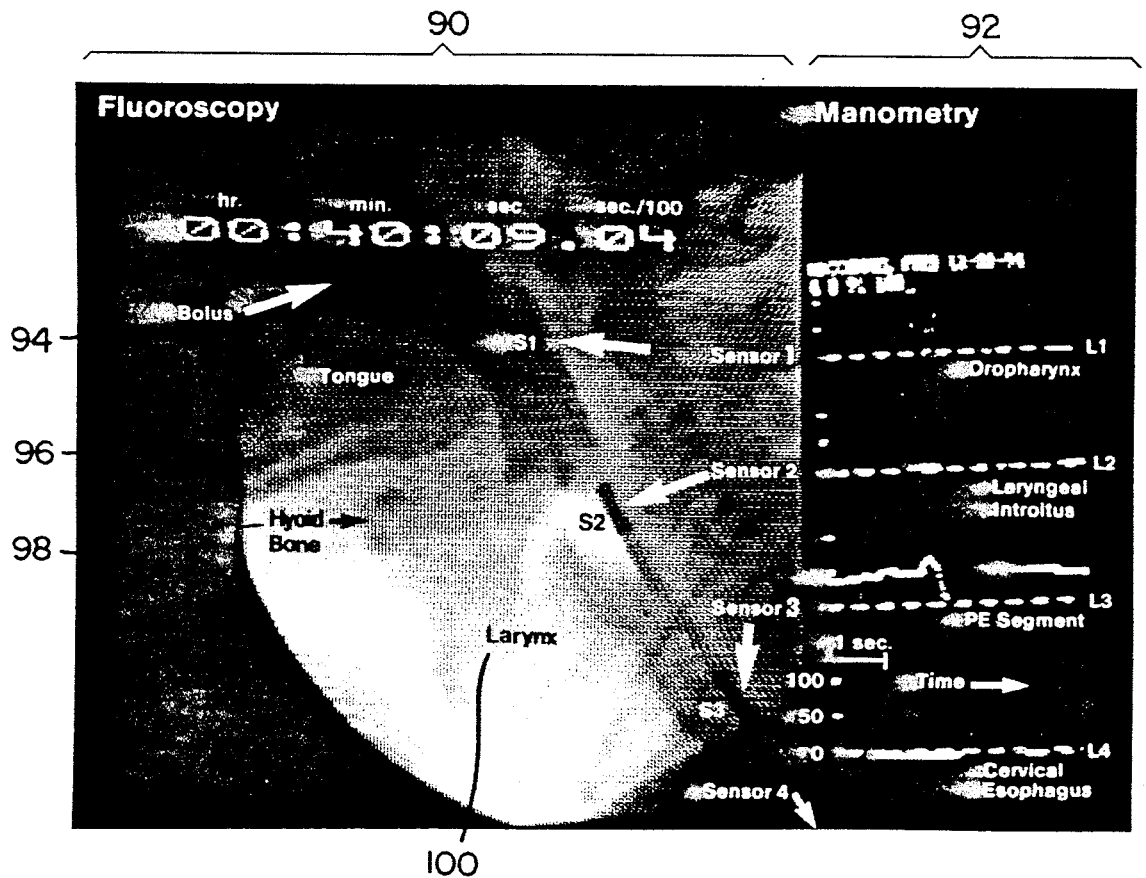
Figure 6:
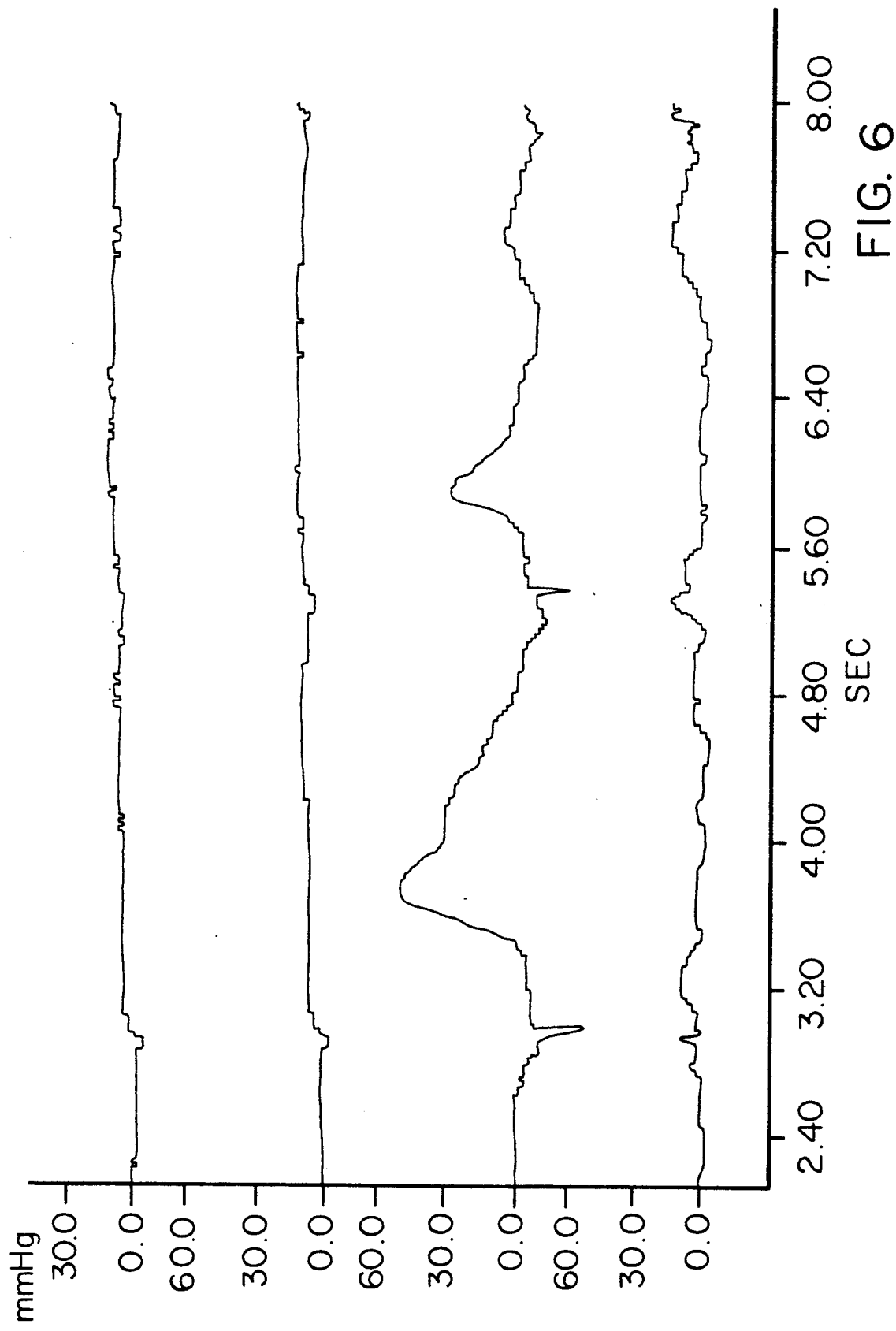
Figure 8:
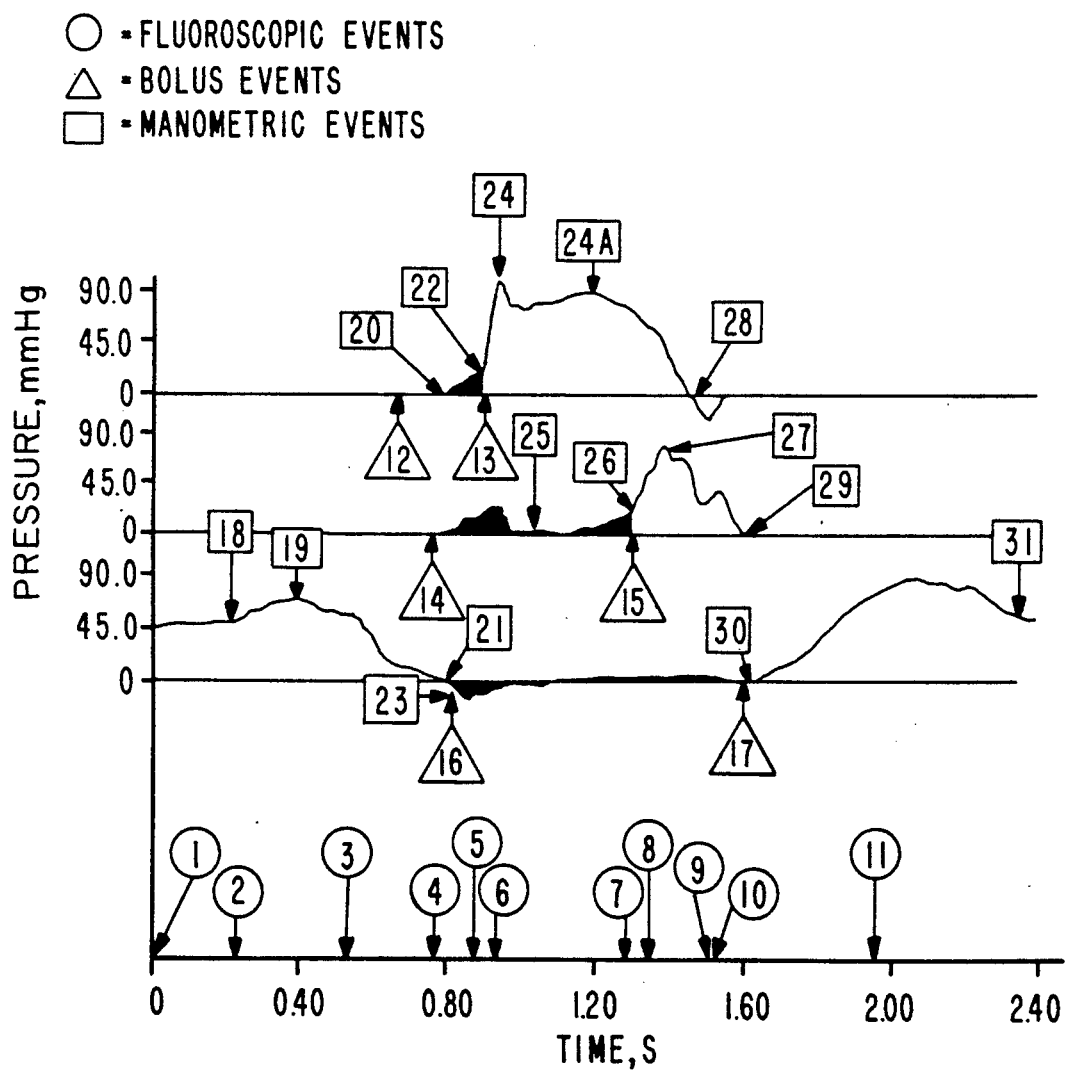
Figure 9:
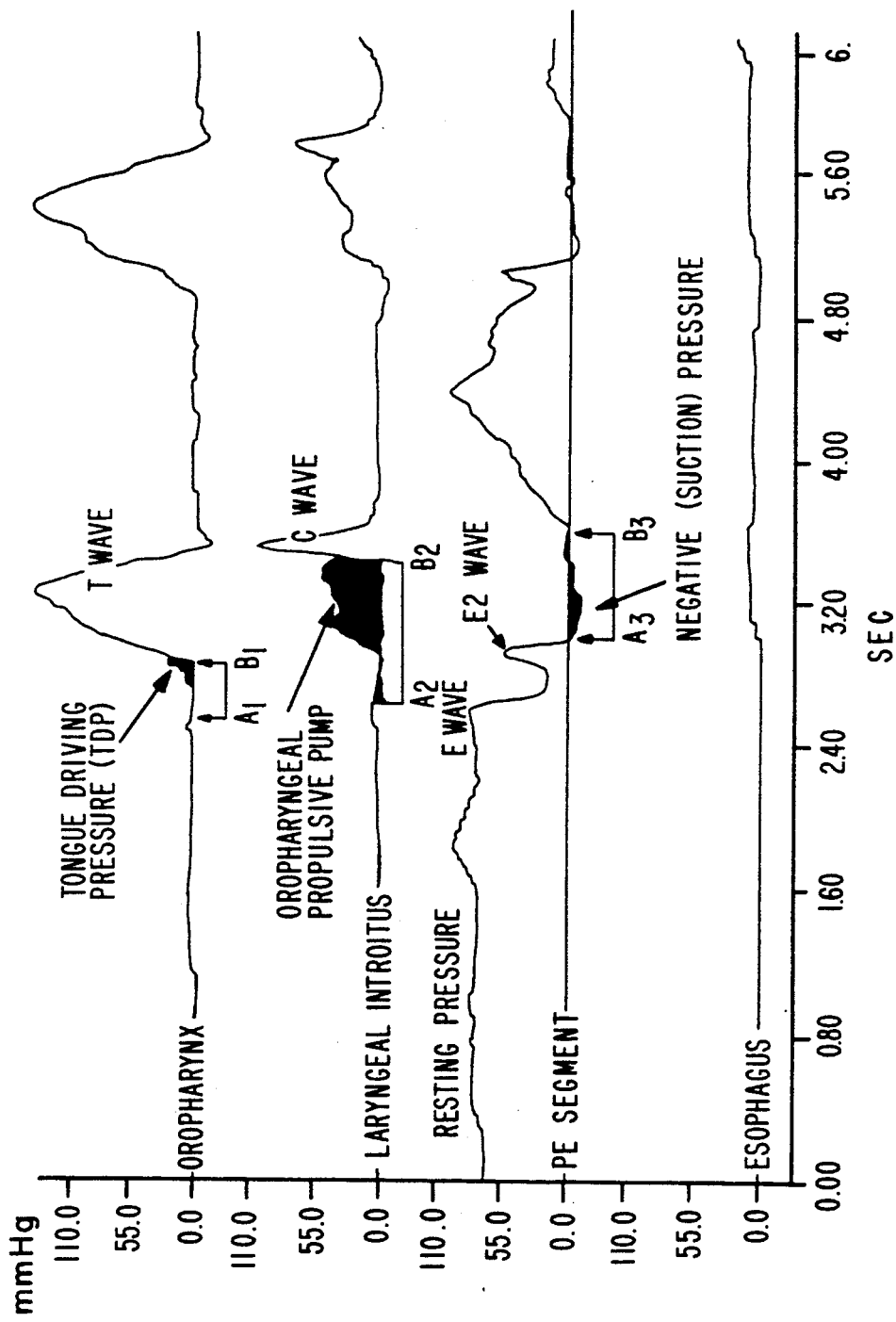

A 62-year-old male with Wallenberg's syndrome with aspiration is presented in FIG. 9, along with a summation of data determined from program 28, except that aspiration and bolus residue are manually entered to program 28 from program 54. The barium swallow showed residual barium above the PE segment with aspiration after each swallow. Manometry in FIG. 9 show an altered PE segment pressure complex. The manofluorogram shows that the initial onset of the PE segment pressure decline was delayed in relation to the generation of the oropharyngeal pressure. After the pressure decline, there was an extra, uncoordinated contraction in the PE segment during the relaxation phase. This is indicated as E2 in FIG. 9. Note the increase in the OPPF due to the obstructive E2 wave in the PE segment. This abnormal PE segment contraction interfered with negative pressure generation, causing delayed bolus flow. This contraction delayed the bolus flow for 180 to 200 msec. This abnormal PE segment contraction resulted in a decreased hypopharyngeal suction pump force of −0.5 mu (normal=2.1). With this PE pressure obstruction, an increased oropharyngeal propulsion pump (OPP) force of 23.8 mu (normal=3.3) and an increased tongue driving force of 13.7 mu (normal=1.5) occurred. When aspiration occurred, it was due to inadequate clearing of the bolus from the pharynx before the larynx reopened. Extended cricopharyngeal myotomy was recommended for this extra, obstructing pharyngeal contraction in the PE segment.

Case 2

Figure 10:
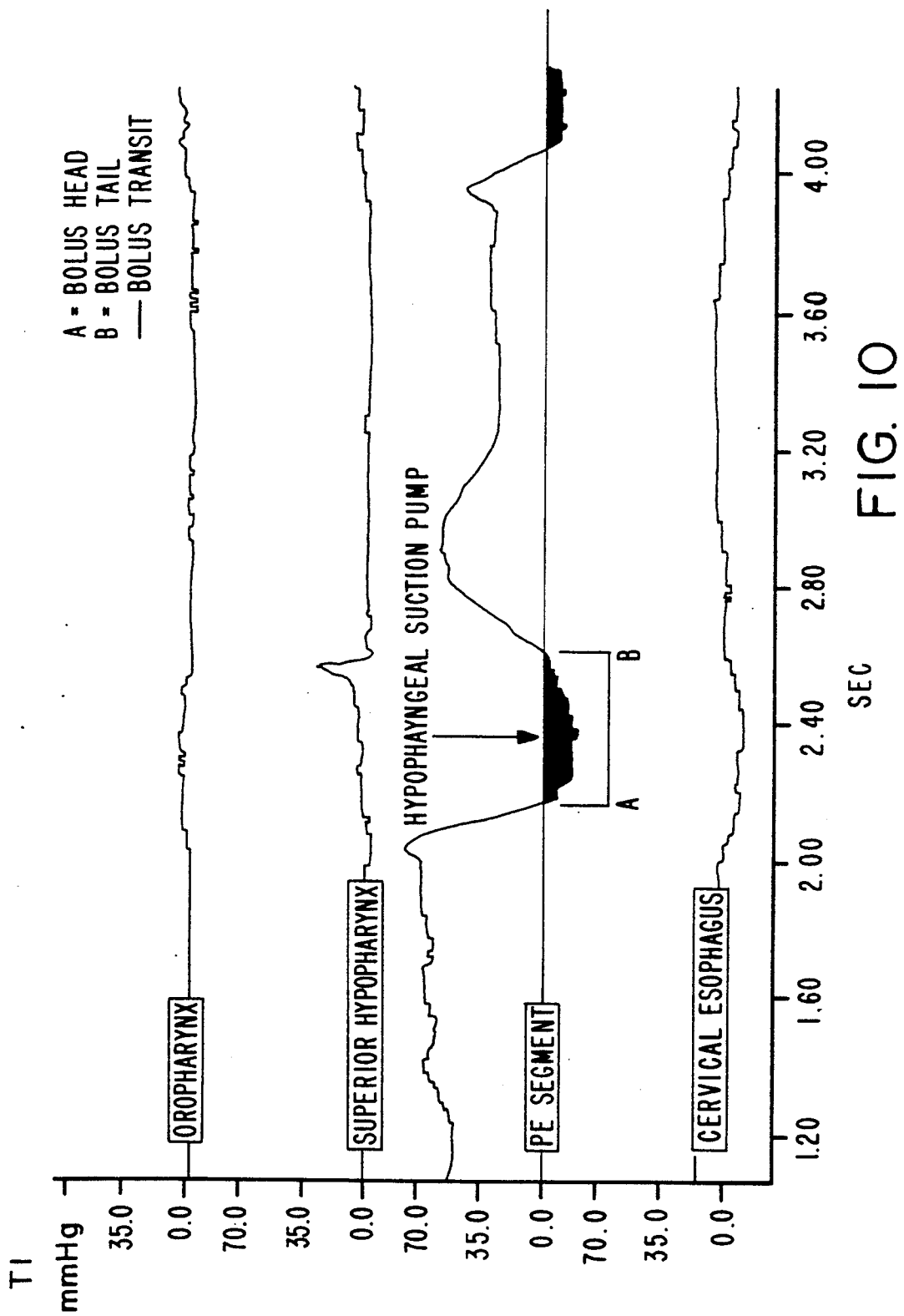
FIG. 10 is a representation of a manofluorogram of an individual with Guillain-Barre syndrome.

A 32-year-old male with dysphagia and aspiration secondary to Guillain-Barre syndrome is presented in FIG. 10. He received regular feeding via a nasogastric tube. A barium swallow showed massive aspiration with pooling of barium in the pyriform sinuses. Manometry showed a normal PE segment complex. The manofluorogram showed that the only effective pressure generator was the PE segment. No tongue driving pressure or oropharyngeal propulsion pump force was measured. The negative PE segment pressure was developed by repeated swallows, which partially elevated the larynx. Bolus flow occurred only during the periods of laryngeal elevation of PE negative pressure. Hypopharyngeal suction force was −2.7 mu (in contrast to normal readings of −2.1). When the PE segment pressure reached 0 mm Hg or higher, all bolus flow ceased. Aspiration occurred only if the bolus size exceeded the volume of the pyriform sinuses, and then it occurred only after the larynx had reopened. Because the hypopharyngeal suction pump is the only bolus driving force, a CP myotomy was not recommended.

Case 3

Figure 11:
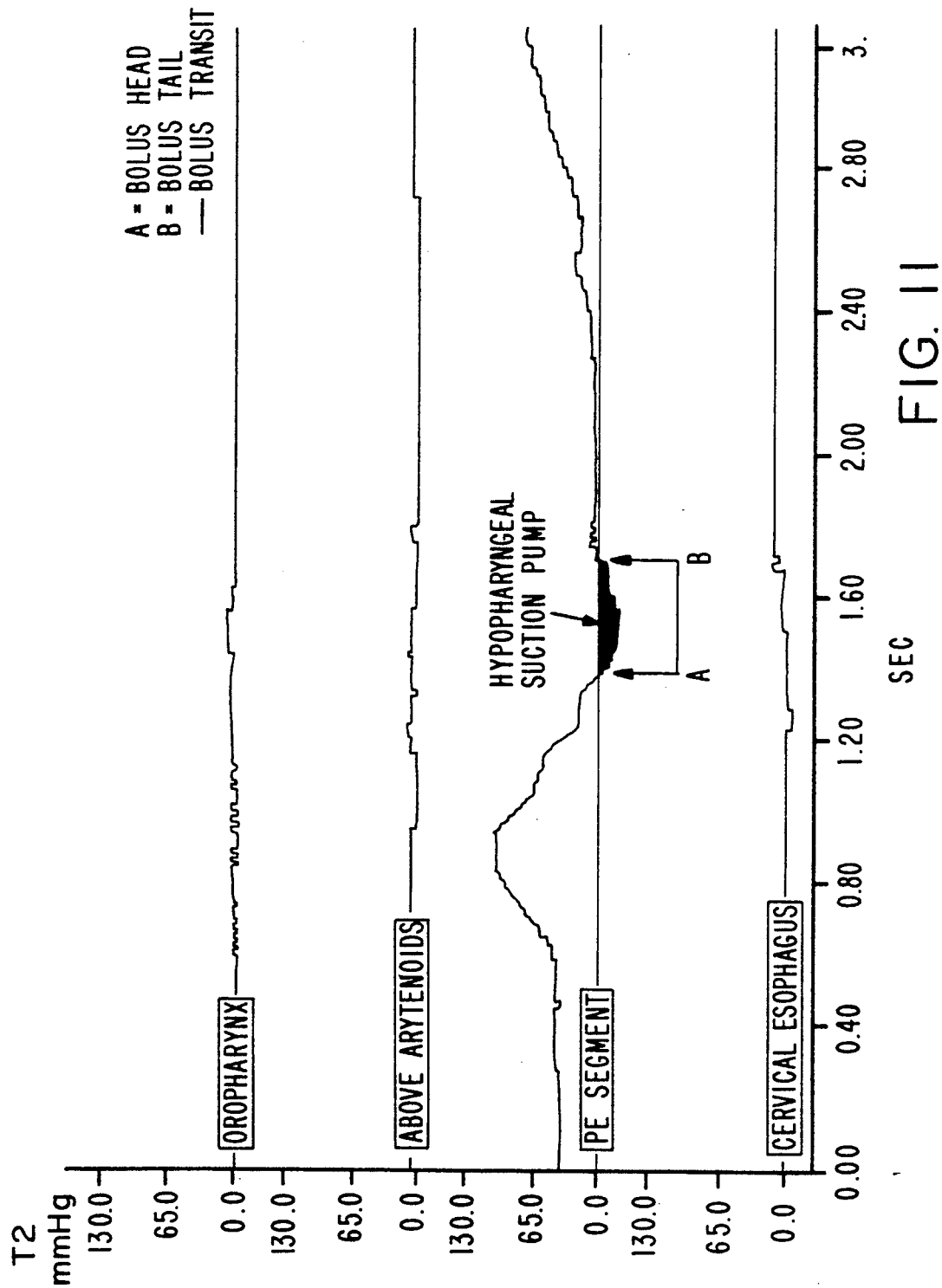
FIG. 11 is a representation of a manofluorogram of an individual with oculopharyngeal muscular dystrophy.

A 70-year-old male who had a several-year history of progressive swallowing difficulties and aspiration is presented in FIG. 11. An hour was required to eat a normal meal. He was referred with a diagnosis of cricopharyngeal achalasia for a cricopharyngeal myotomy. The barium swallow showed the cricopharyngeal muscle obstructing bolus flow. Standard manometry showed a normal PE segment complex. The manofluorogram demonstrated that the major abnormality was in the oropharynx. The PE segment function was primarily responsible for this patient's swallowing. The hypopharyngeal suction pump force was −2.2 mu. There was no tongue driving force or oropharyngeal propulsion pump force. Based on the findings of manofluorography, with the absence of a T wave pressure and a C wave, the diagnosis was changed from cricopharyngeal achalasia to oculopharyngeal muscular dystrophy syndrome, a genetic and progressive disease. The proposed treatment—a cricopharyngeal myotomy—was rejected as wholly inappropriate because this was the only effective mechanism for pressure gradient generation for bolus flow.

Case 4

Figure 12:
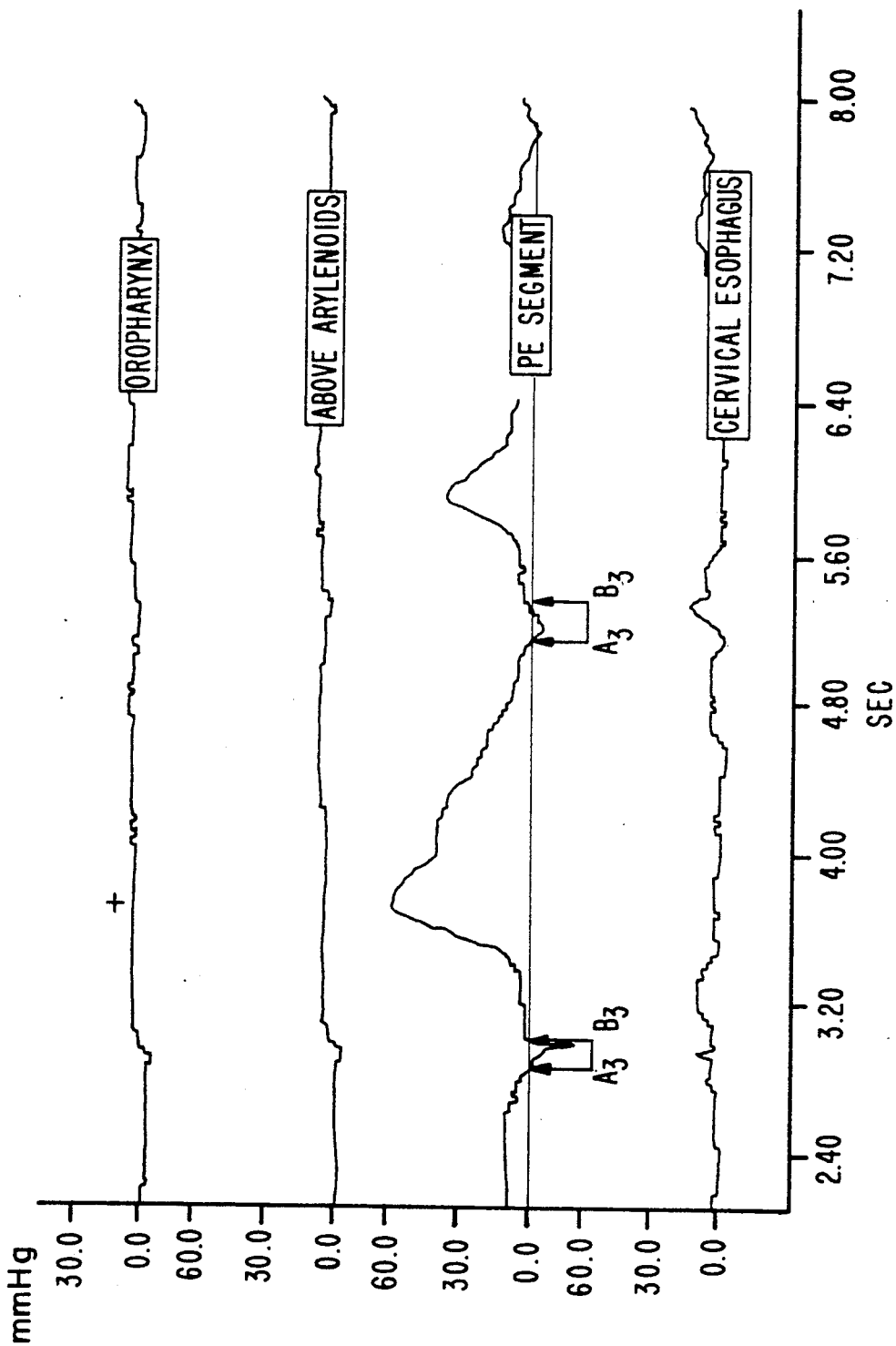
FIG. 12 is a representation of a manofluorogram of an individual with irradiation fibrosis.

FIG. 12 presents a 72-year-old male with a chief complaint of dysphagia and aspiration. The patient had undergone a radical neck dissection and irradiation of a tongue-base carcinoma 14 years previously. Aspiration had been present for 4 months, resulting in a recent pneumonia. A barium swallow showed massive aspiration and pooling of barium above the PE segment. Standard manometry showed a normal PE segment pressure pattern. The manofluorogram showed no tongue driving pressure, no oropharyngeal propulsion pump force, and a reduced hypopharyngeal suction pump force of —0.7 mu. Radiation fibrosis had impaired both tongue motion and laryngeal elevation. With both functional pressure gradient generators impaired, the dysfunction resulted in aspiration, and the patient required feeding by gastrostomy.

Case 5

Figure 13:
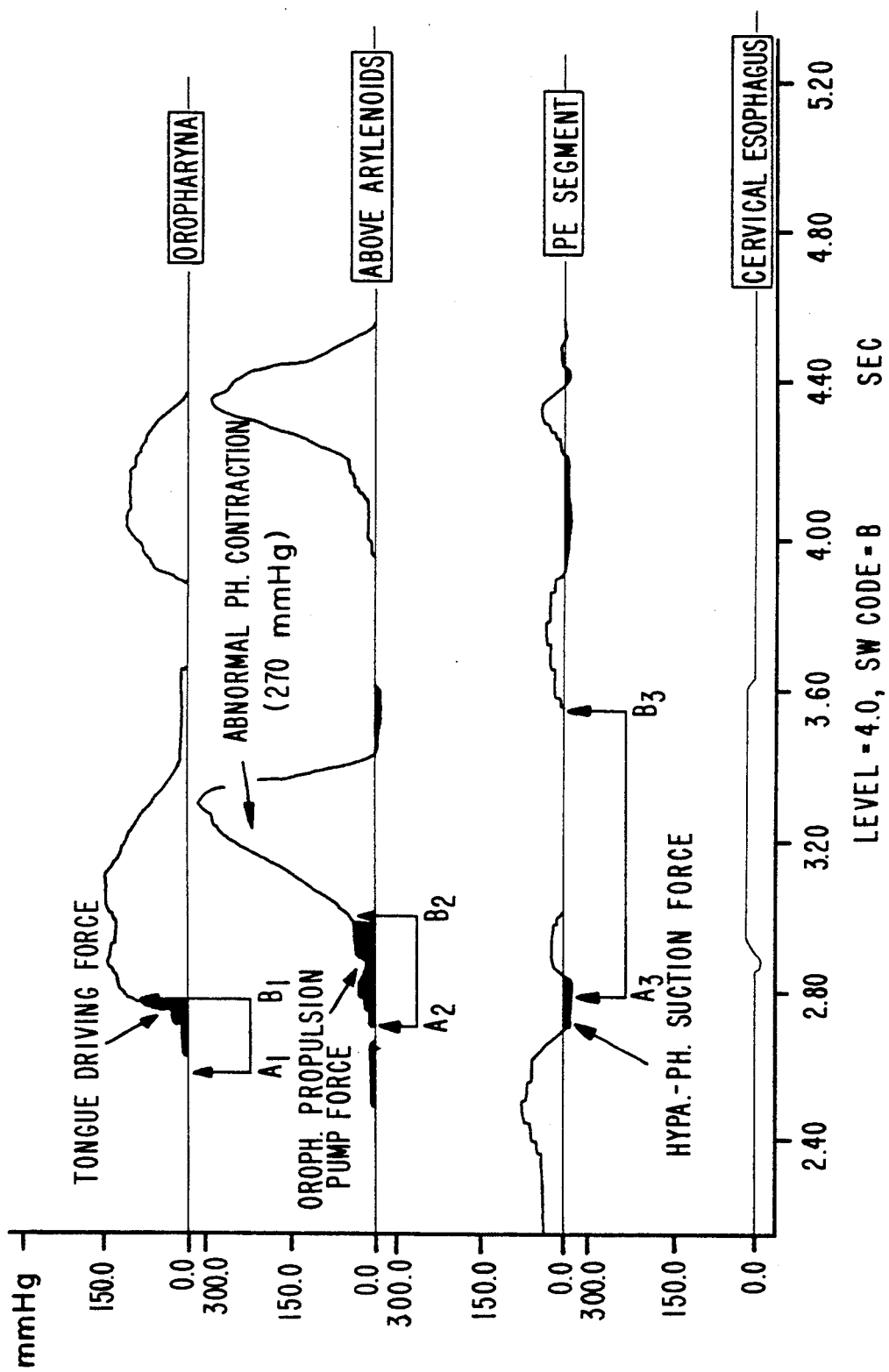
FIG. 13 is a representation of a manofluorogram of an individual with pharyngeal dysphagia.

FIG. 13 shows a 39-year-old female with the diagnosis of globus hystericus. Her chief complaint was that for several years, upon swallowing, she felt "a lump in the throat." The patient had a thyroidectomy 6 years previously. The previous work-up consisted of a normal barium swallow and a normal-appearing PE segment pattern on standard manometry. The manofluorogram showed an abnormal pharyngeal contraction, with pressure ranging from 270 to 360 mm Hg, recorded at the laryngeal introitus. These abnormal contraction pressures occurred after the bolus tail had passed, but this abnormal contraction did not delay bolus passage. In fact, the pharyngeal transit time was faster than normal (804 msec vs. 835 msec for normal patients). The tongue driving force was normal. However, the oropharyngeal propulsion pump force was increased (7.8 mu vs. 3.3 mu for normal patients). The hypopharyngeal suction pump force was decreased to —0.7 mu (in contrast with 2.1 mu for normal patients). The diagnosis was changed from globus hystericus to abnormal pharyngeal contraction. A neurological consultation was requested. The patient has not been retested after medical treatment.

Case 6

Figure 14:
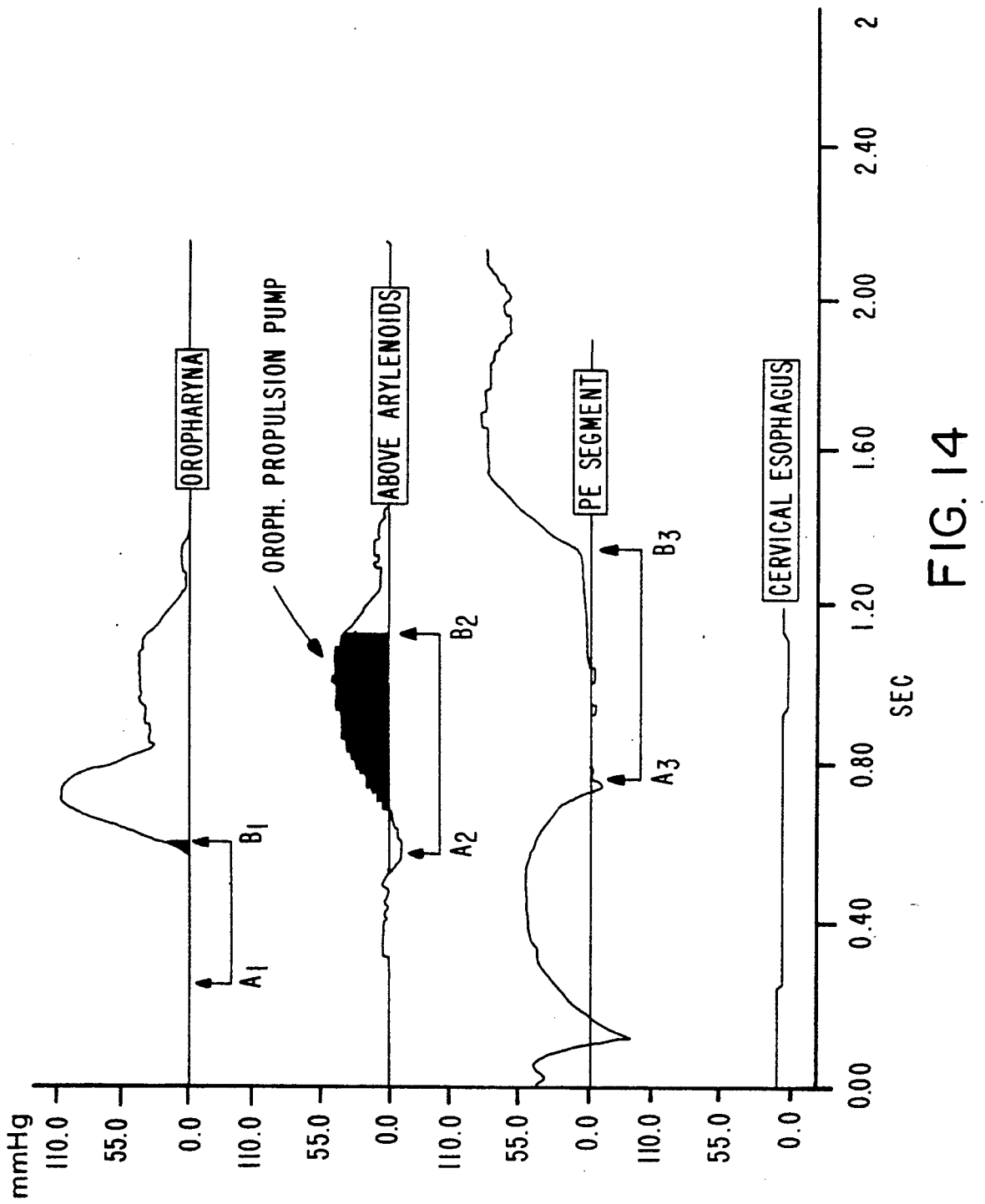
FIG. 14 is a representation of a manofluorogram of an individual with dermatomyositis.
Figure 4:
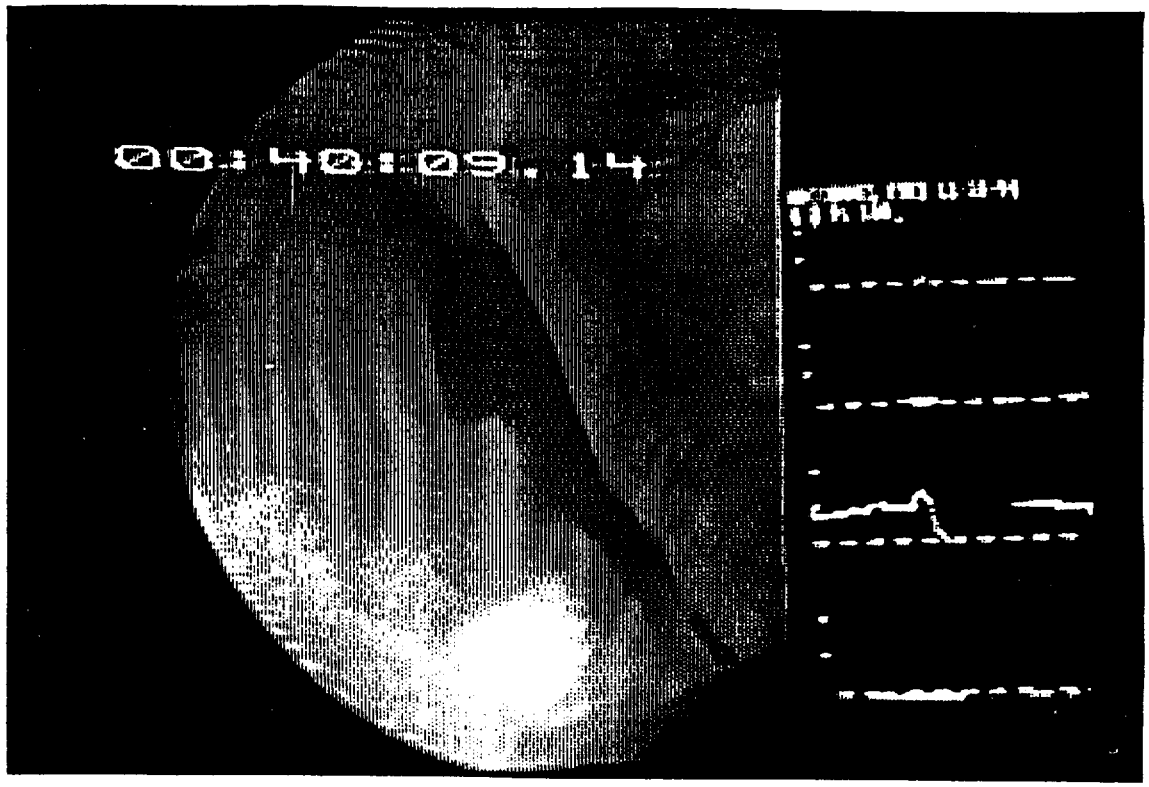

FIG. 14 presents a 70-year-old female with a chief complaint of muscular weakness, dysphagia, and aspiration. The previous workup consisted of a reported normal standard manometry of the PE segment and a barium swallow with moderate aspiration. The most notable finding on the manofluorogram was an abnormal positive pressure wave of up to 70 mm Hg during the PE segment relaxation phase. This pressure obstructed bolus flow above the PE segment. Due to this obstructed bolus flow, an increased oropharyngeal propulsion force (21.2 mu vs. 3.3 mu for normal patients) was recorded. After the obstructive pressure wave, there was a period of negative pressure during which bolus flow occurred. The hypopharyngeal suction pump force was —0.7 mu (vs. —2.1 mu in normal patients). In the superior hypopharynx, no pharyngeal constrictor pressures were seen during the swallow. The only pressure recorded at the level of the laryngeal introitus was the transmitted pressure wave generated in the oropharynx. The lack of pharyngeal contraction caused impaired clearing of the bolus. On several swallows, the abnormal pressure wave of the PE segment exceeded the pressure of the oropharynx. This caused the bolus to flow in a retrograde manner back into the oropharynx. Three to four repeated swallows were required to pass the entire bolus into the esophagus. A muscle biopsy was consistent with a diagnosis of dermatomyositis. A myotomy was recommended. After myotomy, the patient was tested again. Pre-bolus obstructing pressure in the PE segment was not recorded postmyotomy. The bolus residue was still present after swallowing but was significantly reduced.

The case presentations are summarized in Table 3.

TABLE 3

| Parameters | Normal | Wallenberg's | SUMMARY Guillian-Barre | Ocul. Ph. Dys. | Irrad. Fibrosis | Dermatomyositis | Ph. Dysphagia |
|---|---|---|---|---|---|---|---|
| Tongue driving force | 1.5 | 13.7 | 0 | 0 | 0 | * | * |
| Oropharynegeal propulsion | 3.3 | 23.8 | 0 | 0 | 0 | 21.2 | 7.8 |
| Hypopharyngeal suction pump | —2.1 | —0.5 | —2.7 | —2.2 | —0.7 | —0.7 | —0.1 |
| Pharyngeal transit time | 835 msec | 1,160 msec | >1 min | >1 min | >1 min | 950 msec | 804 msec |
| Bolus residue | 0 | 25% | 100% | 100% | 75% | 30% | 0 |
| Aspiration | 0 | 0 | ++ | + | +++ | 0 | 0 |

These cases show that a major pharyngeal pressure generator for developing a pressure gradient is the PE segment. A negative pressure is generated with laryngeal elevation and opening of the PE segment before bolus arrival. Bolus flow can be obstructed in the PE segment by three different mechanisms: (1) lack of laryngeal elevation; (2) lack of cricopharyngeal muscle relaxation; and (3) extra constrictor contraction in the PE segment. These mechanisms are demonstrated in the above case reports.

With the manofluorogram, abnormal pressure can be correlated with bolus flow. In the dermomyositis patient of case 6, the abnormal PE segment contraction pressure exceeded the driving pressure from the oropharynx, resulting in retrograde flow of the bolus from the hypopharynx to the oropharynx. This is an example of the bolus flow responding to a pressure gradient.

The two patients in cases 2 and 4 did not elevate the larynx, causing PE segment bolus obstruction. In cases where there is extra muscular contraction, a myotomy could potentially aid this problem. However, not enough of these patients have been tested postoperatively to substantiate the effects of myotomy.

In the patient with oculopharyngeal muscular dystrophy in case 3, manofluorogram analysis changed the diagnosis and treatment. The patient was referred with cricopharyngeal aclasis for a myotomy. Manofluorogram analysis showed that the PE segment pressure was the only effective pressure generator for this patient's swallowing. The oropharyngeal pressure and C wave pressure were not produced. In this patient, fluoroscopy made it appear that PE segment dysfunction was responsible for the problem because the bolus flow was delayed above the PE segment, and there was a bulge at the point of cricopharyngeal muscle. However, the pressure gradient defect was the absence of propulsive driving force from the oropharynx and not PE segment dysfunction. A cricopharyngeal myotomy was not done on the patient.

Cases 1, 4 and 6 illustrated PE segment obstruction to bolus flow. If the output of a pump is obstructed, then the pressure will rise until the output obstruction is overcome. In the two cases—dermatomyositis and Wallenberg's syndrome—an increased propulsion pressure is recorded at the level of the laryngeal introitus.

If there is no tongue driving pressure generated in the oropharynx, as seen in the cases of tongue immobility due to irradiation and the Guillain-Barre syndrome, no oropharyngeal propulsive pressure is generated.

In conclusion, the invention described herein is considered pioneering in nature. Thus, a good deal of further research and development needs to be done. Nonetheless, these beginnings represent an improvement over prior approaches to understanding, diagnosing, and treating disorders in the digestive tract, and patients have been helped thereby.

I claim:

1. A system for forming a combined magnetic recording of (a) the location and movement of a radiopaque bolus in a patient's alimentary tract over a period of time and (b) data indicating pressures exerted on said bolus during said period of time, the system comprising:
    a catheter carrying a plurality of radiopaque pressure sensors for inserting in an alimentary tract, each said sensor for outputting electronic signals in response to the application of pressure to the sensor, said signals being reflective of the amount of said pressure;
    means for processing said electronic signals so as to output a series of first magnetically recordable signals representative of a plurality of synchronized graphs (one graph for each said sensor) of pressure-versus-time data points that indicate the magnitude and timing of the pressures experienced by said sensors;
    videofluoroscopy means for producing a series of second magnetically recordable signals representative of a series of images of at least a portion of an alimentary tract and a radiopaque bolus situated therein over a period of time; and
    means for recording both said series of first and second magnetically recordable signals on a single magnetic medium, in such a manner that the resultant combined recording can be played back to simultaneously display on the same monitor screen said images and said graphs in the same sequence in which they were created, with each said displayed image lagging by less than 0.1 second the last-entered pressure-versus-time data point in each graph appearing therewith on the screen.

2. The system of claim 1, wherein the electronic signals output by each said sensor are analog electronic signals, and wherein said signal processing means comprises:
    means operatively connected to said sensors for amplifying said electronic signals,
    means operatively connected to said amplifying means for filtering said amplified signals,
    means operatively connected to said filtering means for converting said filtered signals to digital signals, and
    a digital computer programmed to receive said first digital signals, process them, and generate signals representative of said plurality of synchronized graphs.

3. The system of claim 1, further comprising:
    means for including a record of time on said combined recording in such a manner that the combined recording, when played back, simultaneously displays said time on the same monitor screen as said images and said synchronized graphs.

4. The system of claim 3, wherein the electronic signals output by each said sensor are analog electronic signals, and wherein said signal processing means comprises:
    means operatively connected to said sensors for amplifying said electronic signals,
    means operatively connected to said amplifying means for filtering said amplified signals,
    means operatively connected to said filtering means for converting said filtered signals to digital signals, and
    a digital computer programmed to receive said first digital signals, process them, and generate signals representative of said plurality of synchronized graphs.

5. The system of claim 1, wherein said sensors are solid state.

6. The system of claim 5, wherein said catheter carries at least four of said sensors for inserting in an adult human's throat, and further wherein said sensors are arrayed on said catheter in such locations that when a first of said sensors is opposite an adult human patient's tongue base, a second of said sensors will be substantially opposite the patient's introitus of the larynx, a third of said sensors will be substantially opposite the patient's pharyngo-esophageal segment, and a fourth of said sensors will be substantially opposite the patient's cervical esophagus.

7. The system of claim 6, wherein the electronic signals output by each said sensor are analog electronic signals, and wherein said signal processing means comprises:
    means operatively connected to said sensors for amplifying said electronic signals,
    means operatively connected to said amplifying means for filtering said amplified signals,
    means operatively connected to said filtering means for converting said filtered signals to digital signals, and
    a digital computer programmed to receive said first digital signals, process them, and generate signals representative of said plurality of synchronized graphs.

8. The system of claim 1, wherein said recording means comprises:
    mixing means operable to receive said series of first and second magnetically recordable signals and generate a video signal which, when displayed on a monitor, generates a split screen in which said images appear in one section and said synchronized graphs appear in a separate section; and
    a video cassette recorder operatively connected to said mixing means for creating a recording of said video signal.

9. The system of claim 8, wherein the electronic signals output by each said sensor are analog electronic signals, and wherein said signal processing means comprises:
- means operatively connected to said sensors for amplifying said electronic signals,
- means operatively connected to said amplifying means for filtering said amplified signals,
- means operatively connected to said filtering means for converting said filtered signals to digital signals, and
- a digital computer programmed to receive said first digital signals, process them, and generate signals representative of said plurality of synchronized graphs.

10. The system of claim 1, wherein the recording means produces a combined recording which, when played, creates a screen display in which each said displayed image is essentially contemporaneous with the last-entered pressure-versus-time data point in each said graph appearing therewith on the screen.

11. The system of claim 10, wherein the electronic signals output by each said sensor are analog electronic signals, and wherein said signal processing means comprises:
- means operatively connected to said sensors for amplifying said electronic signals,
- means operatively connected to said amplifying means for filtering said amplified signals,
- means operatively connected to said filtering means for converting said filtered signals to digital signals, and
- a digital computer programmed to receive said first digital signals, process them, and generate signals representative to said plurality of synchronized graphs.

12. The system of claim 10, further comprising:
- means for including a record of time on said combined recording in such a manner that the combined recording, when played back, simultaneously displays said time on the same monitor screen as said images and said synchronized graphs.

13. The system of claim 12, wherein the electronic signals output by each said sensor are analog electronic signals, and wherein said signal processing means comprises:
- means operatively connected to said sensors for amplifying said electronic signals,
- means operatively connected to said amplifying means for filtering said amplified signals,
- means operatively connected to said filtering means for converting said filtered signals to digital signals, and
- a digital computer programmed to receive said first digital signals, process them, and generate signals representative of said plurality of synchronized graphs.

14. The system of claim 10, wherein said sensors are solid state.

15. The system of claim 14, wherein said catheter carries at least four of said sensors for inserting in an adult human's throat, and further wherein said sensors are arrayed on said catheter in such locations that when a first of said sensors is opposite an adult human patient's tongue base, a second of said sensors will be substantially opposite the patient's introitus of the larynx, a third of said sensors will be substantially opposite the patient's pharyngo-esophageal segment, and a fourth of said sensors will be substantially opposite the patient's cervical esophagus.

16. The system of claim 15, wherein the electronic signals output by each said sensor are analog electronic signals, and wherein said signal processing means comprises:
- means operatively connected to said sensors for amplifying said electronic signals,
- means operatively connected to said amplifying means for filtering said amplified signals,
- means operatively connected to said filtering means for converting said filtered signals to digital signals, and
- a digital computer programmed to receive said first digital signals, process them, and generate signals representative of said plurality of synchronized graphs.

17. The system of claim 10, wherein said recording means comprises:
- mixing means operable to receive said series of first and second magnetically recordable signals and generate a video signal which, when displayed on a monitor, generates a split screen in which said images appear in one section and said synchronized graphs appear in a separate section; and
- a video cassette recorder operatively connected to said mixing means for creating a recording of said video signal.

18. The system of claim 17, wherein the electronic signals output by each said sensor are analog electronic signals, and wherein said signal processing means comprises:
- means operatively connected to said sensors for amplifying said electronic signals,
- means operatively connected to said amplifying means for filtering said amplified signals,
- means operatively connected to said filtering means for converting said filtered signals to digital signals, and
- a digital computer programmed to receive said first digital signals, process them, and generate signals representative of said plurality of synchronized graphs.

19. A method for forming a combined magnetic recording of (a) the location and movement of a radiopaque bolus in a patient's alimentary tract over a period of time and (b) data indicating pressures exerted on said bolus during said period of time, the method comprising the steps of:
- inserting into the alimentary tract of said patient a catheter carrying a plurality of radiopaque pressure sensors, each said sensor being operable to output electronic signals in response to the application of pressure to the sensor, said signals being reflective of the amount of said pressure;
- having said patient attempt to swallow said radiopaque bolus;
- processing electronic signals output by said sensors during said attempted swallow so as to produce a series of first magnetically recordable signals representative of a plurality of synchronized graphs (one graph for each said sensor) of pressure-versus-time data points that indicate the magnitude and timing of the pressures experienced by said sensors;
- videofluoroscoping said alimentary tract of said patient during said attempted swallow so as to produce a series of second magnetically recordable signals representative of a series of images of at least a portion of said alimentary tract and said radiopaque bolus situated therein over a period of time; and recording both said series of first and second magnetically recordable signals on a single magnetic medium to form a combined recording that can be played back to simultaneously display on the same monitor screen said images and said graphs in the same sequence in which they were created, with each said displayed image lagging by less than 0.1 second the last-entered pressure-versus-time data point in each graph appearing therewith on the screen.

20. The method of claim 19, wherein the catheter used is one that carries at least four of said sensors arrayed on said catheter in such locations that, for an adult patient, when a first of said sensors is opposite said patient's tongue base, a second of said sensors will be substantially opposite the patient's introitus of the larynx, a third of said sensors will be substantially opposite the patient's pharyngo-esophageal segment, and a fourth of said sensors will be substantially opposite the patient's cervical esophagus, and said catheter is so inserted in the alimentary tract as to locate the first of said sensors opposite the tongue base.

21. The method of claim 19, wherein the step of recording produces a combined recording which, when played, creates a screen display in which each said displayed image is essentially contemporaneous with the last-entered pressure-versus-time data point in each said graph appearing therewith on the screen.

22. The method of claim 19, further comprising the step of:

including a record of time on said combined recording in such a manner that the combined recording, when played back, simultaneously displays said time on the same monitor screen as said images and said synchronized graphs.

23. The method of claim 19, wherein said sensors carried on said catheter are solid state pressure sensors.

24. The method of claim 19, wherein said step of recording comprises:

mixing said series of first and second magnetically recordable signals to generate a video signal which, when displayed on a monitor, generates a split screen in which said images appear in one section and said synchronized graphs appear in a separate section; and recording said video signal by video cassette recorder means.

25. The method of claim 19, wherein said step of processing comprises:

amplifying said electronic signals output by each said sensor, said output signals being analog electronic signals;

filtering said amplified signals;

converting said filtered signals to digital signals, and receiving in a programmed digital computer said digital signals, processing them, and generating signals representative of said plurality of synchronized graphs.

26. The method of claim 25, wherein the catheter used is one that carries at least four of said sensors arrayed on said catheter in such locations that, for an adult patient, when a first of said sensors is opposite said patient's tongue base, a second of said sensors will be substantially opposite the patient's introitus of the larynx, a third of said sensors will be substantially opposite the patient's pharyngo-esophageal segment, and a fourth of said sensors will be substantially opposite the patient's cervical esophagus, and said catheter is so inserted in the alimentary tract as to locate the first of said sensors opposite the tongue base.

27. The method of claim 25, wherein the step of recording produces a combined recording which, when played, creates a screen display in which each said displayed image is essentially contemporaneous with the last-entered pressure-versus-time data point in each said graph appearing therewith on the screen.

28. The method of claim 25, further comprising the step of:

including a record of time on said combined recording in such a manner that the combined recording, when played back, simultaneously displays said time on the same monitor screen as said images and said synchronized graphs.

29. The method of claim 25, wherein said sensors carried on said catheter are solid state pressure sensors.

30. The method of claim 25, wherein said step of recording comprises:

mixing said series of first and second magnetically recordable signals to generate a video signal which, when displayed on a monitor, generates a split screen in which said images appear in one section and said synchronized graphs appear in a separate section; and recording said video signal by video cassette recorder means.

31. A method for preparing a swallowing profile record of a human patient by use of a combined magnetic recording of (a) the location and movement of a radiopaque bolus in said patient's alimentary tract over a period of time and (b) data indicating pressures exerted on said bolus during said period of time, wherein the recording can be played back to simultaneously produce a video display on the same monitor screen of images of said bolus in said tract, of elapsed time, and of the magnitude of pressure being exerted in at least one location in the tract, with each said displayed image lagging by less than 0.1 second the pressure magnitude, the method comprising:

playing said combined magnetic recording on video display means;

measuring from the video display of said played combined magnetic recording a transit time for said radiopaque bolus to move a distance between one location and another location in said patient's alimentary tract;

computing from the video display of said data indicating pressures and from said transit time a force acting on said bolus; and forming a record of said force acting on said bolus to produce said swallowing profile record of said human patient.

32. The method of claim 31, wherein said step of measuring said transit time includes:

measuring at least one transit time selected from the group consisting of: pharyngeal transit time, oropharyngeal transit time, and hypopharyngeal transit time.

33. The method of claim 31, further comprising the steps of:

computing a velocity of the bolus from the transit time and the distance; and entering data representing said velocity on said record.

34. The method of claim 33, wherein the step of computing a velocity includes:
   computing at least one velocity selected from the group consisting of: average pharyngeal bolus head velocity, oropharyngeal bolus head velocity, and hypopharyngeal bolus head velocity.

35. The method of claim 31, wherein said step of computing a force includes:
   computing a force selected from the group consisting of: tongue driving force, transmitted tongue driving force, pharyngeal clearing force, and hypopharyngeal suction pump force.

36. The method of claim 35, further comprising the steps of:
   computing a second force selected from the group consisting of: tongue driving force, transmitted tongue driving force, pharyngeal clearing force, and hypopharyngeal suction pump force; and
   entering on said record said second force acting on said bolus to produce said swallowing profile record of said human patient.

37. The method of claim 36, further comprising the steps of:
   computing a third force selected from the group consisting of: tongue driving force, transmitted tongue driving force, pharyngeal clearing force, and hypopharyngeal suction pump force; and
   entering on said record said third force acting on said bolus to produce said swallowing profile record of said human patient.

38. The method of claim 37, further comprising the steps of:
   computing a fourth force selected from the group consisting of: tongue driving force, transmitted tongue driving force, pharyngeal clearing force, and hypopharyngeal suction pump force; and
   entering on said record said fourth force acting on said bolus to produce said swallowing profile record of said human patient.

* * * * *

UNITED STATES PATENT AND TRADEMARK OFFICE
CERTIFICATE OF CORRECTION

PATENT NO. : 5,024,240                                   Page 1 of 3
DATED      : June 18, 1991
INVENTOR(S): Fred M.S. McConnel It is certified that error appears in the above-identified patent and that said Letters Patent is hereby corrected as shown below:

The Drawing Sheet, consisting of FIG. 4, should be added as shown on the attached page.

Column 7, last line, the table entry "a:" is corrected to read -- a:\mandatla\ --.

Column 8, first line in table, the word "mandatla" is deleted.

Column 14, last line, the following text is added after "of": -- each value is divided by its mean to quickly find the relative variance of the values.--.

UNITED STATES PATENT AND TRADEMARK OFFICE
CERTIFICATE OF CORRECTION

PATENT NO.    : 5,024,240

DATED         : June 18, 1991

INVENTOR(S)   : Fred M.S. McConnel

It is certified that error appears in the above-identified patent and that said Letters Patent is hereby corrected as shown below:

Column 15, Table 1, in entry No. 3, "tone" is changed to -- bone --; in entry No. 27, "ave" is changed to -- wave --.

Column 17, in the footnote to Table 2 the symbol "Pe" is changed to --PE --.

Column 25, line 35, the word "to" is changed to -- of --.

Signed and Sealed this

Sixteenth Day of February, 1993

Attest:

STEPHEN G. KUNIN

*Attesting Officer*      *Acting Commissioner of Patents and Trademarks*